(12) United States Patent
Jesperson et al.

(10) Patent No.: US 6,806,058 B2
(45) Date of Patent: Oct. 19, 2004

(54) SECRETIONS OF PROTEINS BY ENCAPSULATED CELLS

(75) Inventors: Diana Jesperson, Malvern, NJ (US); Yevgenya Akselband, Brighton, MA (US); Patricia McGrath, Cambridge, MA (US); Jan Trnovsky, Saugus, MA (US); Phillip T. Moen, Foxborogh, MA (US)

(73) Assignee: One Cell Systems, Inc., Cambridge, MA (US)

( * ) Notice: Subject to any disclaimer, the term of this patent is extended or adjusted under 35 U.S.C. 154(b) by 0 days.

(21) Appl. No.: 10/157,351

(22) Filed: May 28, 2002

(65) Prior Publication Data

US 2003/0143642 A1 Jul. 31, 2003

Related U.S. Application Data

(60) Provisional application No. 60/293,822, filed on May 26, 2001.

(51) Int. Cl.$^7$ .............................................. G01N 33/53
(52) U.S. Cl. .................. 435/7.5; 435/7.21; 435/7.9; 435/188; 435/287.2; 436/63; 436/532; 436/823
(58) Field of Search ........................... 435/7.4, 7.5, 7.9, 435/188, 287.2; 436/63, 532, 823

(56) References Cited

U.S. PATENT DOCUMENTS

| | | | |
|---|---|---|---|
| 4,801,529 A | | 1/1989 | Perlman |
| 4,959,301 A | | 9/1990 | Weaver et al. |
| 5,225,332 A | | 7/1993 | Weaver et al. |
| 5,888,728 A | | 3/1999 | Olson et al. |
| 5,965,379 A | * | 10/1999 | Tamarkin et al. .......... 435/7.93 |
| 6,068,979 A | * | 5/2000 | Akavan-Tafti ................ 435/6 |

FOREIGN PATENT DOCUMENTS

WO    WO 01/40455 A1    6/2001

OTHER PUBLICATIONS

Holmes et al. Improved cell line development by a high throughput affinity capture surface display technique to select for high secretors. J. Immu. Methods (1999) 230: 141–147.*

Akselband, Y., "Cytokine Secretion in Mixed Cell Populations," abstract of grant No. IR43A143774–01 for National Institute of Allergy and Infectious Diseases (1998).

Gray et al., "Secretion capture and report web: use of affinity derivatized agarose microdroplets for the selection of hybridoma cells," *J. Immunological Methods* , 182(2):155–163 (1995), MEDLINE abstract only, ACC No. 95310745.

Hadas et al., "A Rapid and sensitive heterogeneous immunoelectrochemical assay using disposable electrodes," *J. of Immunoassay*, 13(2):231–252 (1992), MEDLINE abstract only, ACC No. 93055465.

* cited by examiner

*Primary Examiner*—Long V. Le
*Assistant Examiner*—Jacob Cheu
(74) *Attorney, Agent, or Firm*—Townsend and Townsend and Crew, LLP

(57) ABSTRACT

The invention provides methods of analyzing a secreted protein from a cell encapsulated in a microdrop. The microdrop is formulated with biotinylated matrix molecules at a reduced ratio of biotin to matrix molecules compared with previous formulations. The reduced ratio is advantageous for improving the resolution of detection and allows simultaneous detection of multiple secreted proteins and/or multiple cell surface markers. The invention further provides inter alia methods of isolating IgG isotype antibodies that have switched from IgM isotype.

42 Claims, 8 Drawing Sheets

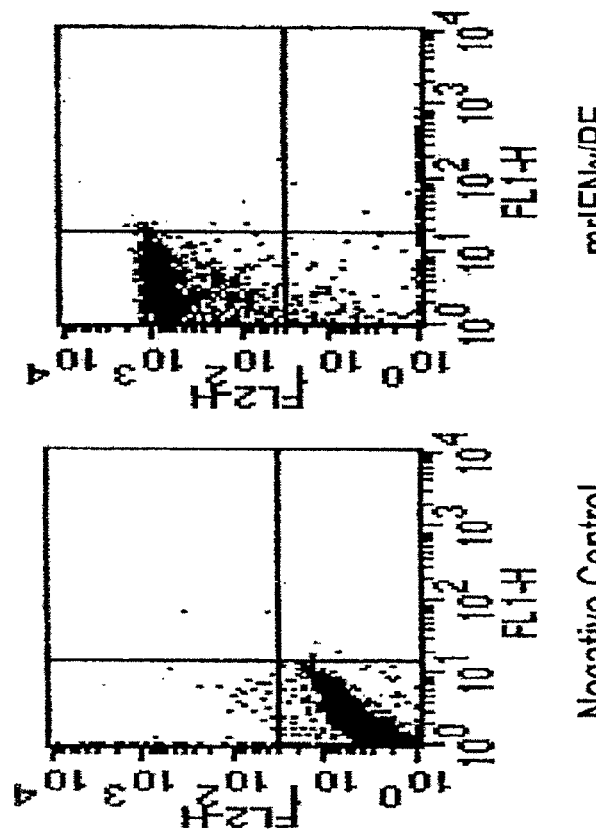
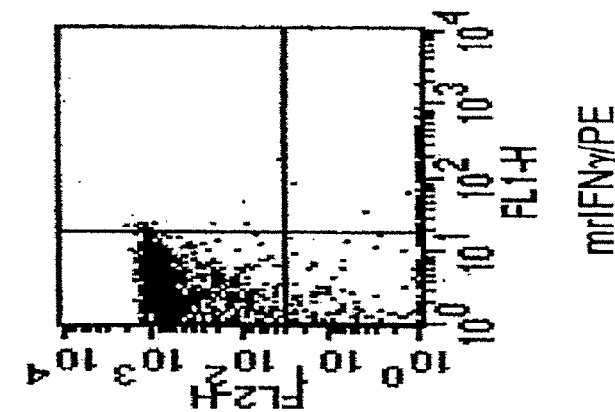
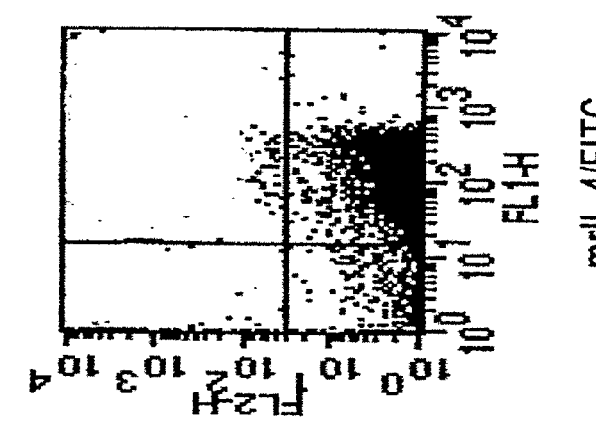
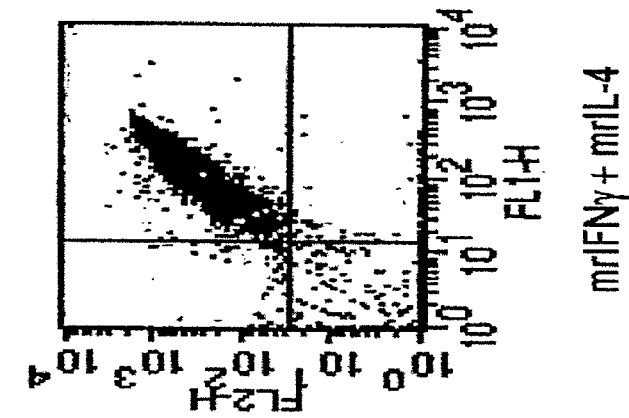
FIG. 6A  Negative Control
FIG. 6B  mrIFNγ/PE
FIG. 6C  mrIL-4/FITC
FIG. 6D  mrIFNγ + mrIL-4

Unstimulated PBMCs | Stimulated PBMCs

SECRETIONS OF PROTEINS BY ENCAPSULATED CELLS

CROSS-REFERENCE TO RELATED APPLICATIONS

The present application derives priority from U.S. Ser. No. 60/293,822 filed May 26, 2001, which is incorporated by reference in its entirety for all purposes.

BACKGROUND

The gel microdrop (GMD) secretion assay involves encapsulating cells in a biotinylated matrix, followed by capture and detection of cell-secreted molecules with fluorescent markers (17–34). This technology differs from other encapsulation methods in that the small size of the microdrop (e.g., <50 μm diameter) creates a defined microenvironment around the cell without impeding diffusion of nutrients, antibodies, or nucleic acid probes into the microdrops, or diffusion of secreted products. Furthermore, microdrops can readily be analyzed using flow cytometry and sub-populations can be detected. The number of occupied cells in each microdrop preparation depends on the number of cells used for encapsulation and is approximated by Poisson statistics for single cell encapsulation (19). To obtain microdrops having a high probability of initially containing 0 or 1 cells, an experimental protocol has been developed in which 1–1.5 million cells are encapsulated in 20 million microdrops, resulting in approximately 5–10% single cell occupation . . . . The emulsion is transiently cooled, causing the drops to gel. Once gelled, the microdrops are physically distinct and robust and can be removed from the oil into an aqueous medium by low speed centrifugal separation. Since the microdrop agarose matrix is a permeable semi-solid support, immunochemical procedures can be performed on encapsulated cells.

SUMMARY OF THE CLAIMED INVENTION

The invention provides methods of analzying a secreted protein. Such method entail encapsulating a cell in a microdrop wherein the microdrop comprises matrix component molecules, first biotin molecules linked to the matrix component molecules, capture molecules with affinity for a molecule secreted by the cell linked to second biotin molecules, and streptavidin linking the first and second biotin molecules, the first biotin molecules and the matrix component molecules being in a molar ratio of less than 0.85, preferably 0.01 to 0.2, and optionally 0.02–0.2 moles biotin per mole matrix component molecules. The molecule is secreted from the cell and binds to the capture molecules is thereby retained within the microdrop. The secreted molecule is then detected. In some methods the concentration of the first biotin molecules in the microdrop is less than or equal to 42 micromolar.

In some methods, the encapsulating step encapsulates a plurality of cells in the microdrop. In some methods, the encapsulating step encapsulates a single cell in the microdrop. In some methods, the secreted molecule is a protein, hormone, or carbohydrate. In some methods, the streptavidin and capture molecules are encapsulated into the microdrops at the same time as the cell. In some methods, the streptavidin and captured molecules are incorporated into the microdrop after the encapsulating step. In some methods, the microdrop further comprises second capture molecules with affinity for a second secreted molecule, the second capture molecules being linked to additional copies of the second biotin molecules. In some methods, the cell secretes the second molecule. In some methods, the detecting step is performed by contacting the microdrop with a detection reagent having affinity for the secreted molecule, and detecting binding of the detection reagent to the secreted molecule. In some methods, the detection reagent is labeled. In some methods, a signal of the labeled detection reagent bound to the secreted molecule is proportional to the number of copies of the secreted molecule within the microdrop. In some methods, the detecting step is performed by contacting the microdrop with a first detection reagent having specific affinity for the secreted molecule and a second detection reagent having specific affinity for the second secreted molecule, wherein the first and second detection reagents are differentially labeled. In some methods, the cell secretes a third secreted molecule, and the microdrop further comprises third capture molecules with affinity for the third secreted molecule, the third capture molecules being linked to additional copies of the second biotin molecules, and the method further comprises contacting the microdrop with first, second, third and fourth detection reagents having specific affinity for the secreted molecule, the second secreted molecule, the third secreted molecule and a cell surface marker respectively, and the detecting step detects the secreted protein, the second secreted protein, the third secreted protein and the cell surface marker. In some methods, the detection step is performed by contacting the microdrop with a first detection reagent having affinity for the secreted molecule and a second detection reagent having affinity for a cell surface marker, and the first and second detection reagents are differentially labeled. In some methods, the detection reagent and the capture molecules bind to different epitopes on the secreted molecule. In some methods, the matrix component is agarose. In some methods, the secreted protein is an antibody. In some methods, the secreted protein is an antibody of IgG isotype and the capture molecules are antibodies specific for the IgG isotype. In some methods, the secreted protein is a cytokine. Some methods further comprise inducing the cell to secrete the secreted molecule. In some methods, the inducing is performed after the encapsulating step. In some methods, the inducing is performed before the encapsulating step.

In some methods, the cell comprises a vector comprising a nucleic acid segment encoding the secreted protein, the segment being operably linked to one or more regulatory DNA segments that effect expression of the secreted protein. In some methods, the secreted protein is naturally secreted by the cell. Some methods further comprise a step of propagating the cell to form a cell line after the detecting step. In some methods, the cell was obtained from a patient. In some methods, the cell is a cytotoxic T-cell. Some methods further comprise introducing a population of cells resulting from propagating the cell into the patient. In some methods, the cell is a stem cell. In some methods, the patient is suffering from an autoimmune disease and the cell is a Th2 cell. In some methods, the cell is an islet cell secreting insulin and the patient is in a prodromal period prior to onset of clinical symptoms. Some methods further comprise treating the cell with IL-10 during the propagating step. Some methods further comprise separating the cells from other cells using a cell sorter based on a fluorescent signal resulting from binding of a fluorescently labeled detection reagent to the secreted molecule. In some methods, the cell secretes first and second proteins, and the matrix comprises first and second capture molecules with affinity for the first and second proteins respectively, and the analyzing step comprises contacting the cell with first and second detection reagents that bind to the first and second secreted proteins, and detecting the first and second proteins from signal of the first and second detecting reagents bound to the first and second secreted proteins.

The invention provides methods of analyzing a population of cells. Such methods entail encapsulating a population of cells in microdrops. The cells are contacted with a first detection reagent for a first marker, and a second detection reagent for a second marker, wherein the first marker is a secreted protein and the second marker is a cell surface protein or a second secreted protein. Cells having both the first and second markers are detected. In some methods, at least some microdrops encapsulate single cells. Some methods further comprise separating the microdrops encapsulating the cells from unoccupied microdrops on a Percoll, polysucrose, sodium diatrizoate, or iodixanol gradient. Some method further comprise forming an array of microdrops encapsulating the cells attached to a solid support, and wherein the detecting is performed using a scanning fluorescent, colorimetric, chemiluminescent detector. Some methods further comprise contacting the microdrops encapsulating cells with an agent, and wherein the detecting indicates whether the agent affects the level of the secreted protein.

In some methods, the encapsulated cells are population of cells from a patient and the agent is a different population of cells from the patient. In some methods, the sub-population of cells is isolated by binding of fluorescently labelled antibody to a cell surface marker, and detection of the fluorescent signal. In some methods, the population of cells are obtained from a patient and the presence of the cells having both the first and second markers indicates an immune status of the patient. In some methods, the cells are antigen-specific T-cells. In some methods, the first and second markers are selected from the group consisting of IL-4, IL-10, IFNgamma and TNFalpha. In some methods, the first and second particular proteins are selected from the group consisting of IL-10 and IL-12. In some methods, the identified cells are Th1 cells. In some methods, the identified cells are Th2 cells. In some methods, the second marker is a cell surface marker of T-cell differentiation. In some methods, one of the markers is CD4 or CD8.

The invention further provides methods of analyzing a population of cells. Such methods entail encapsulating a population of cells expressing proteins in microdrops, and wherein the microdrops comprise matrix component molecules, first biotin molecules linked to matrix component molecules, at least first capture molecules having affinity for an epitope in at least one type of secreted protein; the first capture molecules being linked to second biotin molecules, and streptavidin, linking the first and second biotin molecules; whereby proteins are secreted from the cells and proteins having affinity for the first capture molecules are captured within the microdrops; and analyzing the secreted proteins within the microdrops. In some methods, at least some of the microdrops encapsulate a single cell. In some methods, the cells secrete the same protein at different levels, and the analyzing step compares the levels. In some methods, the cells secrete different proteins, and the analyzing step detecting a cell secreting a particular protein. In some methods, the population of cells was obtained from the patient, and the analyzing identifies a subpopulation of cytotoxic T-cells and the method further comprises reintroducing the population of cells without the subpopulation of cells into the patient. In some methods, the patient is suffering from or susceptible to an autoimmune disease, graft versus host disease or host versus graft disease. Some methods further comprise treating the population of cells without the subpopulation of cells with IL-10 before the reintroducing step.

The invention further provides a population of microdrops encapsulating cells, and the microdrops comprise matrix component molecules, first biotin molecules linked to the matrix component molecules, capture molecules with affinity for a protein secreted by the cell linked to second biotin molecules, and streptavidin linking the first and second biotin molecules, the first biotin molecules and the matrix molecules being in a molar ratio of less than 0.85, preferably less than 0.01–0.2, and optionally less than 0.02–0.2 moles biotin per mole matrix component molecules. In some populations at least some microdrops encapsulate a single cell.

The invention further provides in a method of analyzing a protein secreted by a cell in which the cell is encapsulated with a microdrop comprising biotinylated agarose the improvement wherein the molar ratio of biotin to agarose is less than 0.85, preferably 0.01 to 0.2, and optionally 0.02 to 0.2 moles biotin per mole agarose.

The invention further provides methods of analyzing a secreted protein. Such methods entail encapsulating a cell in a microdrop wherein the microdrop comprises matrix component molecules, $Ni^{2+}$NTA linked to the matrix component molecules, capture molecules with affinity for a molecule secreted by the cell linked to a hexahistidine tag, wherein the molecule is secreted from the cell and binds to the capture molecules thereby being retained within the microdrop; and contacting the cell with a detection reagent that binds to the secreted molecule wherein the detection reagent.

The method further provides methods of analyzing a secreted protein. Such method entail encapsulating a cell in a microdrop wherein the microdrop comprises matrix component molecules linked to biotin, streptavidin linked to Ni2+ and capture molecules with affinity for a molecule secreted by the cell linked to a hexahistidine tag, wherein the molecule is secreted from the cell and binds to the capture molecules thereby being retained within the microdrop; and contacting the cell with a detection reagent that binds to the secreted molecule wherein the detection reagent.

The invention further provides method s of preparing an antibody of IgG isotype. Such methods entail culturing a population of cells secreting antibodies of IgM isotype under conditions whereby one or more of the cells can undergo isotype switching to IgG isotype; encapsulating the population of cells in microdrops including a capture reagent specific for antibodies of IgG isotype, whereby microdrops containing a cell secreting an antibody of IgG isotype capture the secreted antibody of IgG isotype within the cells; and detecting one or more microdrops containing a cell secreting an antibody of IgG isotype.

In some methods, the cells are cultured in the presence of an agent that stimulates isotype switching. In some methods, the capture reagent is an antibody to the IgG isotype. In some methods, the detecting comprises contacting the microdrops with a detection reagent that binds to the captured antibody at a different site than the capture reagent. In some methods, the detection reagent is an anti-idiotypic antibody. In some methods, the anti-idiotypic antibody is fluorescently labelled. Some methods further comprise isolating the microdrop that has captured the cell secreting the IgG antibody. In some methods, the population of cells are encapsulated in microdrops such that at least some microdrops encapsulate a plurality of cells; and the method isolates a microdrop that has captured a plurality of cells, one or more of which secretes IgG antibody. Some methods further comprise isolating the plurality of cells. Some methods further comprise encapsulating the plurality of cells in microdrops under conditions whereby at least some microdrops encapsulate a single one of the plurality of cells, wherein the microdrops include a capture reagent specific for antibodies of IgG isotype, whereby microdrops containing a cell secreting an antibody of IgG isotype capture the secreted antibody within the microdrops; and detecting one or more microdrops containing a cell secreting an antibody of IgG isotype.

The invention further provides methods for screening a population of cells for a subpopulation having a desired property. Such methods entail (a) encapsulating the population of cells in microdrops at a first ratio of average number of cells per occupied microdrop; (b) screening the encapsulated cells to identify a first subpopulation of microdrops encapsulated cells having the desired property; (c) isolating the cells from the microdrops resulting from the screening step; (d) encapsulating the cells from the screening step at a second ratio of average number of cells per occupied microdrop, the second ratio being smaller than the first ratio; (e) screening the encapulsated cells to identify a second subpopulation of microdrops encapsulating cells having the desired property.

Some methods further comprise repeating steps (c)–(e) at a further ratio of average number of cells per occupied microdrops to isolate a further subpopulation of microdrops.

Some methods further comprise isolating a microdrop encapsulating a single cell from the second subpopulation. In some methods, the subpopulation of cells having the desired property is less than 0.01% of the population of cells before the method is performed.

The invention further provides a kit for making microdrops. Such a kit comprises matrix component molecules linked to biotin, in a molar ratio of less than 0.85, preferably 0.01 to 0.2 and optionally 0.02 to 0.2 moles biotin per mole matrix component molecules. In some kits, the matrix molecules are agarose. Some kits further comprise instructions for using the kit to make microdrops. Some kits further comprise streptavidin and a capture molecule linked to second biotin molecules.

BRIEF DESCRIPTION OF THE FIGURES

FIG. 6. Simultaneous detection of mrIFNγ and mrIL-4 using unoccupied GMDs and flow cytometry. Unoccupied GMDs were made with CelBioGel mrIFNγ (100 ng/ml), mrIL-4 (25 ng/ml) or a mixture of both cytokines were detected using two-color flow cytometry. Dot plots show results: FL-1 (FITC) vs FL-2 (PE) of negative control (panel A), samples incubated with mouse anti-IFNγ/PE (panel B), with mouse anti-IL-4/FITC (panel C), and with a mixture of both Abs (panel D).

DEFINITIONS

Figure 1:
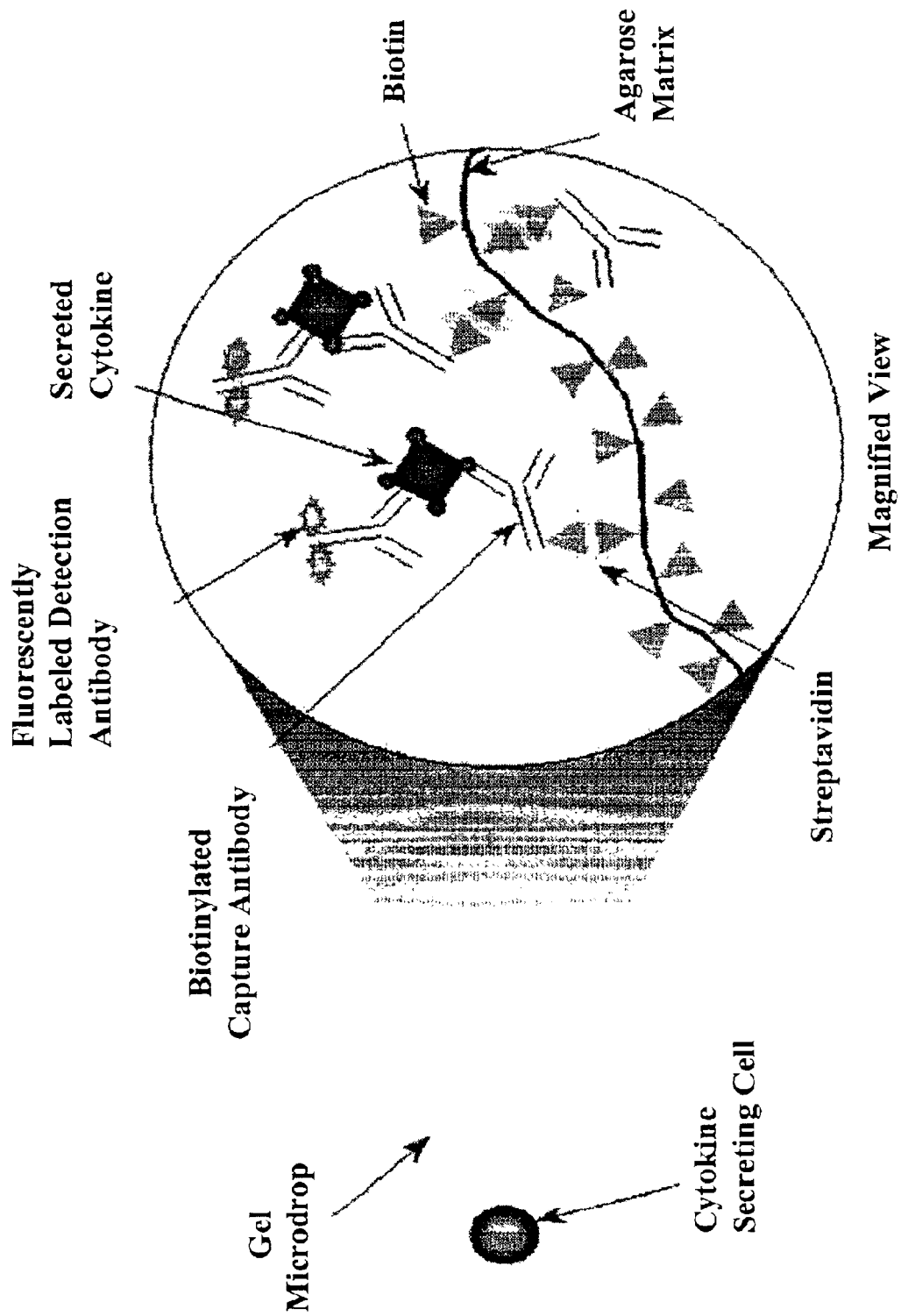
FIG. 1. Capture web for retaining secreted protein in microdrops.

Specific binding or affinity between an antibody or other binding agent and an antigen means a binding affinity of at least $10^6 M^{-1}$. Preferred binding agents bind with affinities of at least about $10^7 M^{-1}$, and preferably $10^8 M^{-1}$ to $10^9 M^{-1}$, $10^{10} M^{-1}$, $10^{11} M^{-1}$, or $10^{12} M^{-1}$. The term epitope means an antigenic determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents.

A capture molecule is an antibody or other molecule that has specific affinity for a polypeptide secreted by a cell.

The terms adhesion molecule and bridging molecule are used to describe components of the linkage between capture molecules and a matrix. The adhesion molecules are linked to the capture molecule and matrix molecule, and the bridging molecule specifically binds to both adhesion molecules forming a bridge between them and thereby linking the capture molecule to the matrix.

Cell surface markers include CD1, CD2, CD3, CD4, CD5, CD8, CD11(a), (b), (c), CD18, CD44, CD45R, CD59, MHC I, II and III, carcinoembryonic antigen, growth factor receptor (e.g., FGFR, PDGFR, EFG, NGFR, and VEGF) G-protein receptors, such as substance K receptor, the angiotensin receptor, the α- and β-adrenergic receptors, the serotonin receptors, and PAF receptor. See, e.g., Gilman, *Ann. Rev. Biochem.* 56:625–649 (1987), ion channels (e.g., calcium, sodium, potassium channels), muscarinic receptors, acetylcholine receptors, GABA receptors, glutamate receptors, and dopamine receptors (see Harpold, U.S. Pat. Nos. 5,401,629 and 5,436,128), and adhesion molecules (see Springer, *Nature* 346:425–433 (1990). Osborn, *Cell* 62:3 (1990); Hynes, *Cell* 69:11 (1992)).

CD markers are widely used in the determination of cell lineage and sublineage. For example, T cells are identified by the expression of CD3. A mature T cell may belong to the T4 subset, in which case, it will express CD4. Similarly, there are markers for other cell populations and subpopulations. Within the lineages, it is helpful to distinguish cells at different stages of differentiation and activation. Differentiation status is particularly useful in the diagnostic analysis of the lymphoid and myeloid malignancies, and in research on the hemopoietic system. Examples include markers for naive or antigen-experienced cells (especially the CD45 isoforms) and molecules such as CALLA (CD9) found on B-lineage precursors, including B lineage acute lymphoblastic leukemia. Activation status is especially interesting in studies of cell function. Activation markers include growth factor receptors such as CD25 (a component of the receptor for IL-2), and molecules whose cellular function is not fully understood, such as CD69 and CD98.

Secreted proteins of interest include cytokines and chemokines, such as interleukins IL-1 through IL-18 for example, tumor necrosis factors α & β, interferons α, β, and γ, transforming growth factor alpha and beta (TGF- and TGF-β), colony stimulating factor (CSF), tumor necrosis factor and granulocyte monocyte colony stimulating factor (GM-CSF). See Human Cytokines: Handbook for Basic & Clinical Research (Aggrawal et al. eds., Blackwell Scientific, Boston, Mass. 1991), hormones, enzymes, antibodies and intercellular messengers. Virtually any protein can be engineered to be secreted by fusion to an appropriate signal sequence.

Three types of CelBioGel used in the examples termed CelBioGel-1, -2, and -3 have molar ratios of biotin to agarose of 1:1, 0.2 to 1, and 0.04 to 1 respectively within the experimental error with which such ratios can be calculated (+/−10%). The total biotin concentration in the matrix should not exceed 42 μM.

Reference to "screening" includes "selection" unless otherwise apparent from the context.

DETAILED DESCRIPTION

I. General

The present invention provides improved methods of analyzing secreted molecules from cells encapsulated in microdrops. These methods are premised in part on the result that the sensitivity of detection of secreted molecules depends on the extent of biotinylation of matrix molecules, and that improved sensitivity is obtained using molar ratios of biotin to agarose of less than 0.85, and/or a final biotin concentrations of less than 42 μM, 42 μM being equivalent to the biotin content as contained in CelBioGel-2 (as defined below) For example, use of a ratio of about 0.01 to 0.2 and optionally 0.02 to 0.2 mol biotin per mol agarose results in an improved sensitivity of detection approaching 10 to 100-fold (see Example 2) compared with a 1:1 ratio.

Although an understanding of mechanism is not required for practice of the invention, it is believed that the improvement results in part from greater uniformity in distribution of capture molecules linked to the biotin throughout the volume of microdrops and availability of a greater number of free capture sites subsequent to the formation of the streptavidin bridge. We believe that there are more free capture sites in agarose with a low biotin ratio because the streptavidin, which has four available binding sites for biotin, is less saturated with biotin molecules present in the matrix. Therefore, in the matrix with a low biotin ratio, more binding sites are available for the biotinylated capture antibodies.

The invention also provides methods of analyzing secreted proteins from encapsulated cells. The improved gel matrix ratios described above are advantageous although not essential for such methods. The new methods involve detecting a secreted protein and at least one other marker, either a second secreted protein or a cell surface marker, from the same cell. The capacity to detect multiple markers on the same cell can provide an indication of the differentiation state of the cell. This information is particularly useful in characterizing populations of cells. For example, the presence of cells having certain combinations of markers within a lymphocyte population can be indicative of an immune status in a patient. The assay can be used to generate antigen-specific clones from patients to study autoimmune disease in vitro, monitor immune status, and generate T cell lines that can be used for immunotherapy. The methods are advantageous in detecting low levels of secreted protein (e.g., 1 fg), and in isolating rare secreting cells (e.g., present as less than 0.1% or 0.0001% of a population) in functional and viable form II. The Capture Web Cells to be analyzed are encapsulated within a capture web (as shown in FIG. 1) within a gel microdrop (microdrop). The capture web includes multiple copies of a matrix molecule that forms a gel and multiple copies of a capture molecule for a secreted protein immobilized in the gel. In some methods, the capture molecule is immobilized via a bridge. For example, the bridge can be formed by first and second adhesive molecules linked to the matrix molecule and the capture molecule respectively, and a bridging molecule that links to the first and second adhesive molecules to each other. The bridge effectively anchors the capture molecule to the matrix. In some methods, the first and second adhesive molecules are both biotin, and the bridging molecule is streptavidin or avidin. In these methods, biotin molecules attached to matrix molecules are referred to as first biotin molecules, and biotin molecules attached to the capture molecule are referred to as second biotin molecules.

The matrix molecule exists in liquid form when heated and solidifies as a gel when cooled. Agarose is an example of such a matrix molecule. Agarose is a mixture of polysaccharide chains having alternating alpha (1–3) and beta (1–4) linkages. Various grades of agarose are available with low melting temperature agarose (Type IX) being preferred. Alginate, carrageenan, or polyacrylamide can also be used as alternatives to agarose.

Other combinations of proteins and small molecules can be used as alternatives to streptavidin (or avidin) and biotin respectively. For example, glutathione S-transferase can be used with glutathione, and maltose binding protein with maltose. Combinations of synthetic proteins and small molecules from combinatorial libraries having mutual affinity for each other can also be used.

In a further variation, a capture molecule is linked to a matrix molecule via a bridge formed from NTA (nitrilotriacetic acid)-$Ni^{2+}$ and a hexahistidine tag linked to the capture molecule. The NTA-Ni—$^{2+}$ is chemically attached to the matrix molecule. Ni-NTA-agarose matrices are available commercially from Qiagen. $Ni^{2+}$ forms strong noncovalent bonds with hexahistidine. The hexahistidine tag can also be attached to the capture molecule by chemical linkage but is more typically synthesized with a protein capture molecule as a fusion protein. In a still further variation, a capture molecule is attached to a matrix molecule via a bridge formed from biotin linked to the matrix molecule, streptavidin (or avidin) linked to $Ni^{2+}$ and a hexahistidine tag linked to the capture molecule. The streptavidin binds to the biotin and the $Ni^{2+}$ binds to the hexahistidine tag. Again, such methods have the advantage that the hexahistidine tag can be linked to the capture molecule as a fusion protein.

As noted, when biotin is used as part of the bridge between capture molecule and matrix, the ratio of matrix molecules to biotin affects the sensitivity of subsequent detection. The molar ratio of biotin molecules to matrix molecules is preferably in the range of 0.01 to 0.2 moles biotin per mole matrix molecule and optionally 0.02 to 0.2 moles biotin per mole matrix molecule (within the extent of experimental error with which the ratio can be measured, typically about +/−10%). The latter ratio is equivalent to a ratio of approximately 0.16 to 1.6 micromoles biotin per gram of agarose. The ratio can be determined by NMR or using a commercially available kit from Pierce. Preparations of biotinylated agarose in various ratios between agarose and biotin are commercially available. The ratio can be decreased by mixing biotinylated agarose with ordinary agarose before drop formation. Alternatively, the ratio of biotin to agarose can be adjusted at the time that the biotin is attached to the agarose. In general, for the other bridging formats discussed above, in which a matrix molecule is linked to an adhesive molecule, and one or more additional molecules, the molar ratios of matrix molecule to adhesive molecule attached to the matrix molecule are the same as the ratios given for an agarose and biotin.

Components of the bridge for capturing secreted molecules, including capture molecules can, in general, be mixed with matrix molecules and incorporated into microdrops at the same time as cells, or can be supplied exogenously after microdrops have formed.

Microdrops formed from agarose or other matrix molecules provide a defined microenvironment around a biological entity. The gel does not impede diffusion and allows analysis of large numbers of individual microdrops using flow cytometry, as well as recovery of microdrops of interest using fluorescence activated cell sorting (FACS™) or automated image scanning and micromanipulation. For single cell encapsulation, the number of cells occupying each microdrop is approximated by Poisson statistics, similar to limiting dilution cloning or Petri dish inoculation. To obtain a preparation with a high probability that each microdrop contains 0 or 1 initial cells, about 5–10% of the microdrops should be occupied. If higher throughput is desired, an increased number of cells should be used for the encapsulation process, resulting in multiple cell occupancy in an initial screen. Cells from a sub-population of microdrops resulting from the screen are then reencapsulated at a lower average number of cells per microdrop and the screening is repeated (see discussion of isolating IgG antibodies for an example of this approach).(Microdrops are prepared by dispersing cells in liquefied biotinylated agarose (or other matrix molecules) into an excess of a hydrophobic fluid to form an emulsion. The emulsion is transiently cooled, causing gelling. Once formed, microdrops are physically distinct and robust and can be removed from the oil into an aqueous medium by low speed centrifugation. Alternatively, microdrops can be formed by passing a mixture of liquefied gel and entities through a pulsating nozzle, such as the printhead of an inkjet printer. Instrumentation for microdrop formation, the CellSys 100™ Microdrop Maker, is a specially designed emulsifier coupled to a high precision motor available from One Cell Systems, Inc. By varying the rotation speed, type and amount of surfactant, and emulsion viscosity, microdrops ranging from 2–200 $\mu$m, for example, can be prepared. The Microdrop Maker currently available from One Cell Systems is efficient for making large numbers of microdrops (e.g., $10^7$), requiring approximately one million biological entities to meet the single occupancy requirement. Sometimes, the microencapsulation procedure, can be miniaturized for encapsulating smaller ample preparations. Vortexing can also be used. Such is useful for some clinical applications in which only small numbers of biological entities are present.

Any type of cells can be encapsulated in the microdrops. For example, the cells can be primary cell cultures or cell lines. The cells can be obtained from patient samples, from natural sources (e.g., sea water or soil) or from genetic engineering experiments (e.g., transformed with vectors expressing recombinant proteins). Vectors provide control sequences such as promoters and enhancers and signal sequences to control expression and secretion of recombinant proteins. Optionally, the promoter used is inducible, such as a metallothionine promoter or an arabinose promoter. Cells populations produced by genetic engineering include cells transformed with nucleic acids encoding unrelated proteins, and cells transformed with nucleic acids representing different variants of the same protein. The variants can be natural (e.g., allelic or species) or induced. The variants can be generated by DNA shuffling technology as described by U.S. Pat. Nos. 5,830,721, 5,811,238, 5,605, 793. The cells can be hybridomas secreting antibodies, natural B cells secreting antibodies or cells transformed with antibody encoding genes so that the transformed cells secrete antibodies. The cells can be from humans, mammals, such as horse, sheep, mice, cows, goats, and pigs, plants, bacteria, or fungi. Cell types include primary cells, lymphocytes, monocytes, macrophages, dendritic cells, chondrocytes, pancreatic cells, beta cells, and stem cells. Many types of cells including particular populations of lymphocytes can be obtained from AllCells, LLC (Foster City, Calif.).

The capture web can be assembled prior to cell encapsulation by adding streptavidin and capture reagent in melted agarose simultaneously with cells. Alternatively, cell encapsulation can also be performed as the first step of the procedure with capture web components being added later. Once microdrops are formed, the rest of the capture web is assembled. For example, if biotin is being used as part of the bridge linking capture molecule to the matrix, one of the additional components of the capture web is a biotinylated capture molecule with affinity for a protein to be detected.

The biotin molecules linked to the capture molecule are referred to as second biotin molecules to distinguish them from the biotin molecules linked to the matrix molecules. The other additional component of the capture web is streptavidin or avidin. This component, which can be added together with capture antibody and cells prior to encapsulation, forms a bridge between the first biotin molecules linked to the matrix and the second biotin molecules linked to the capture molecule. The additional components can be introduced into microdrops by diffusion. That is, these components are introduced into media containing the microdrops and the components diffuse into the microdrops. Typically, the streptavidin or avidin is introduced first followed by the biotinylated capture molecules. Unbound capture molecules can be washed off. As previously discussed, a low ratio of biotin to agarose is advantageous to allow capture molecules to diffuse evenly throughout the microdrops The same principles apply using other types of bridges between the matrix molecule and capture molecule. For example, using NTA-$Ni^{2+}$ to attach hexahistidine-capture molecule, microdrops are formed using a matrix molecule modified to bear NTA-$Ni^{2+}$ and capture molecule linked to its hexahistidine tag is diffused into the complete microdrops.

III. Capture Molecules and Detection Reagents

Various methods of the invention employ both capture molecules and detection reagents. Both capture molecules and detection reagents are designed to have affinity for a protein or other molecule to be detected. (Unless otherwise apparent, procedures applicable to detection of secreted proteins are also applicable to other secreted molecules, such as carbohydrates, and hormones). Capture molecules are distinguished from detection reagents in that capture molecules are part of the capture web in microdrops, and serve to anchor secreted proteins within microdrops. By contrast, detection reagents are typically introduced after proteins have been secreted and anchored to the capture molecule in the capture web. The detection reagent diffuses into the microdrops and binds to a secreted protein linked to the capture web, thereby allowing detection of the secreted protein.

The nature of capture molecules and detection reagents depends on the secreted protein to be analyzed. If for example the secreted protein is a cytokine, then the capture molecule and the detection reagent can both be antibodies that bind to the cytokine. Preferably, the capture molecule and detection reagent are antibodies that bind to different epitopes on the cytokine so that both capture molecule and detection reagent can bind simultaneously. If for example, the secreted protein is an antibody, then the capture molecule can be an anti-idiotypic antibody or an antigen to the antibody. In general, capture molecules and detection reagents can be any molecules that have specific affinity for a secreted protein to be detected. The capture molecules and detection reagents can be natural ligands, synthetic molecules or antibodies for example. Antibodies to large numbers of secreted molecules and cell surface markers are commercially available from BD/Pharmingen, Beckman Coulter, Biosource, and R & D Systems. Often antibodies are commercially available in fluorescently labelled form or labelled with biotin.

In some methods, more than one secreted protein is of interest and multiple capture molecules and detection reagents are used. For example, if two secreted proteins are to be detected, two different capture molecules for the respective secreted proteins, both linked to second biotin molecules, can be introduced into gel microdrops. The two secreted proteins bind to their respective capture molecules in the microdrops. The secreted proteins are then detected using two detection reagents specific for the two secreted proteins. These principals can be extended for simultaneous detection of n secreted proteins using n capture molecules and n detection reagents.

In some methods, a secreted protein is to be detected in combination with a cell surface marker. Examples of such markers include lymphocytic markers, CD4, CD8, as well as growth factor receptors and ion channels. In such methods, a capture molecule and detection reagent is needed for the secreted protein as indicated above. However, the cell surface marker on the cell surface does not require linkage to the capture web. Thus, a capture molecule is not needed for retention of a cell surface marker. The cell surface marker is detected using a detection reagent specific for the cell surface marker.

Typically, detection reagents are labelled or are amenable to labeling indirectly via a secondary detection reagent that binds to the detection reagent. Such labeling can be fluorescence, isotopic, magnetic, and paramagnetic among others. Examples of fluorescent labels include PI, FITC, PE, PC5 (PE-Cy5), ECD (PE-Texas Red), and Cy-Chrome (R-PE) which can be detected using 630, 525 nm, 575 nm, 675 nm, 610 nm, and 650 nm band pass filters. In some methods, the detection reagent is labelled with an enzyme, and the microdrops contain a substrate for the enzyme that is processed to a fluorogenic product. In some methods, the signal from a detection reagent is amplified using a secondary label. For example, a primary detection reagent labelled with fluorescein can be incubated 15–30 min with rabbit anti-fluorescein IgG (Accurate Chemical & Scientific). After washing with PBS buffer, microdrops are incubated for 15–30 min with FITC or phycoerythrin-labelled goat anti-rabbit antibody (Sigma, St. Louis, Mo.). If more than one detection reagent is used, then the different detection reagents are differentially labelled (e.g., using different fluorophores). Molecules used for capture are typically not labelled (other than with the biotin molecules that serve to link them to the capture web).

In some methods, cells are induced to stimulate secretion of proteins. For example, recombinant proteins can be engineered to be expressed from an inducible promoter. Supplying an inducing agent initiates or increases secretion of proteins. Induction can be performed before or after cells are encapsulated into microdrops.

IV. Methods of Assay

Assays are performed by encapsulating populations of cells into biotinylated microdrops. A capture web to retain one or more secreted proteins is then formed within the microdrops. The microdrops are then cultured in media for a period to permit protein secretion to occur. This period is typically from 30 min to 48 hr. In some methods, the period is less than 24, 12, 6 or 1 hr. In general, longer periods of incubation result in more secreted protein and a stronger signal. However, after a certain period of time, all capture molecules of the capture web are saturated with secreted protein and further secreted protein simply leaks from the microdrops and does not lead to a stronger signal. In some methods, the period of incubation is sufficiently long that secreted protein from encapsulated cells with the highest rates of secretion occupies all or most of the capture molecules in the microdrops, and protein secreted from encapsulated cells with lower secretion levels occupy proportionally fewer of the capture molecules in the microdrops. In these circumstances, the strength of signal from various cells in a population is approximately proportional to the secretion levels of the cells. With some cells that have low secretion levels, such as MNCs, crosstalk, or leakage of unbound protein into neighboring cells is never seen. For transfected cells that have high secretion rates, the time for secretion can be adjusted to control crosstalk. Because secretion rates are relatively constant for a particular cell line, once the secretion rate is determined, the optimal time for the secretion assay to avoid crosstalk can be determined.

In a variation of the above method, microdrops containing cells are treated with a drug or agent that is a candidate drug before and/or during the incubation period in comparison with a control population of untreated microdrops containing cells. If comparison between treated and control cells indicates a different level of secretion of a protein of interest, then it can be concluded that the drug or candidate drug affects the level of secretion of this protein. information can be useful in establishing activity of a candidate agent or in determining mechanism of a drug already known to be effective.

In another variation of the above method, cells are stimulated or suppressed with other cells or growth factors or cytokines, prior to transplantation in patients. For example, treatment with IL-10 can be used to suppress undesired inflammatory responses (see WO 97/42324).

After incubation to allow secretion, one or more detection reagents is added, one for each secreted protein or cell surface marker to be detected. The detection reagent binds to a protein to which it has specific affinity that has been captured by the web. After binding of detection reagent(s) and generation of signal, the signal can be detected by a variety of approaches. In one simple approach, microdrops are deposited on a glass or plastic surface, such as a microscope slide, or Petri dish. The microdrops adhere to the support and can be arranged in an array format to facilitate analysis. The microdrops can then be individually examined under a microscope for one of more different labels. Detection can be via fluorescence, chemiluminescence, or color of secreted molecules. Digital imaging systems have made it possible to examine cell activity with increasingly higher resolution. Automated microscope based systems driven by value added software are now common research tools. These systems share a number of common features including: the ability to acquire and store fluorescent images, image enhancement, calibration and thresholding (discrimination) options, and system automation and device control. Microscopic images are digitized into a matrix of small regions called picture elements of pixels. The measurement of the brightness at each pixel is stored and then processed to generate an enhanced image. Image analysis systems are distinctive in the type of processing used for image enhancement and the level of resolution available. For example, a simple scanning imaging system from MetaCyte, as are other laser-based instruments such as laser scanning confocal microscope and laser scanning cytometer (Oncosis and CompuCyte). For the he Oncosis instrument, their proprietary Photosis™ laser-activated dye can be used for applications requiring the destruction of cell secreting a specific protein (e.g., where the secreted protein is a cancer specific protein). Cells of interest can be recovered using micromanipulation.

In other methods, microdrops are analyzed using a flow cytometer. Such an instrument counts the number of labelled microdrops and the number of microdrops lacking a label. If two differentially labelled detection reagents are used, the flow cytometer can count microdrops bearing first label only, microdrops bearing second label only, microdrops bearing both labels, and microdrops bearing neither label. In methods employing larger numbers of labels, still further categories of microdrops can be distinguished. The type of label present indicates the type and level of protein protein(s) secreted. Color compensation can be adjusted for spectral overlap using a color compensation kit such as Cyto-Comp™ Reagent Kit and Cyto-Trol™ Control Cells (Beckman Coulter). Cyto-Comp™ consists of 4 sets of two-color reagents to adjust color compensation for multicolor analysis.

Optionally, if cells are fluorescently labelled, flow cytometry analysis can be followed by sorting to make different populations of encapsulated cells available for further analysis, such as microscopy, cell line generation or DNA isolation. FACs separates individual cells having defined properties, such as presence of one or more particular secreted proteins, or degree of secretion level of one or more particular secreted proteins. Such cells can then be further propagated for further analysis (e.g., to analyze DNA preparations from the cells) or to generate a cell line. In some methods, cells having desired properties are introduced into patients for therapeutic purposes.

Optionally, Percoll (silica particles (15–30 nm diameter) coated with non-dialysable polyvinylpyrrolidone (PVP)), polysucrose (Ficoll) with sodium diatrizoate, or iodixanol (iodinated derivative of benzoic acid) gradient centrifugation can be used to eliminate the majority of unoccupied microdrops from the preparation permitting recovery of mostly (>95%) cell-occupied microdrops. Microdrops are prepared by dispersing cells in molten matrix molecules, such as agarose, then forming an emulsion in an excess of a hydrophobic fluid. This method is particularly useful for analyzing rare secreting cells, cells secreting at low levels, and rare cell sub-populations.

Some methods use gating strategies to focus the detection apparatus on a sub-population of microdrops containing a desired population of cells. For example, forward or side scatter can be used to distinguish occupied from unoccupied microdrops. The occupied microdrops can then be further gated to detect a sub-population of cells having a particular surface marker bound by a fluorescently labeled detection reagent. The gated sub-population of cells can then be analyzed for presence of particular secreted proteins differentially labeled from the surface marker.

Some methods use indirect detection of detection reagent for signal amplification. For example, if the detection reagent is an antibody, it can be detected using a labelled antibody against the Ig isotype of interest. In other methods, an amplification cascade is employed. For example, Tyramide Signal Amplification™ (TSA) technology is described by U.S. Pat. Nos. 5,731,158 and 5,583,001 and kits are available from Perkin Elmer. When this approach is used for detection, the primary detection reagent that binds to captured secreted molecules is a molecule, usually, an antibody labeled with horseradish peroxidase (HRP). The HRP is used to catalyze the deposition and binding of a labelled tyramide in microdrops that bind the HRP-labelled detection reagent. In turn, the label on the tyramide serves as binding sites for a secondary detection reagent that is typically labelled fluorescently, and has affinity for the label on the tryamide.

V. Applications

1. Secretion Levels

The above methods are useful in analyzing mixed populations of cells secreting the same protein to identify one or more individual cells that secrete the protein at a defined level. In some methods, one is interested in identifying and recovering cells that secrete the protein in excess of a defined level. In some methods, one is interested in identifying one or more cells that have maximum secretion rates among a population. These methods are useful for analyzing biological entities for secretion of growth factors, cytokines, antibodies, hormones or other secretory molecules. The methods are also useful for analyzing transformed cells secreting a protein encoded by a construct introduced into the cells by genetic engineering. The methods are also useful for analyzing levels of secretion of proteins from hybridomas or other established cell lines. Isolated cells secreting a protein of interest or a high level of a protein of interest can be used to propagate a cell line for production of the protein of interest. The methods are also useful for isolating populations of antigen-specific T and B cells or to identify cells secreting a protein of interest.

2. Cells Secreting Different Proteins

The methods are also useful for analyzing mixed population of cells in which the cells in the population secrete different proteins. In such methods, the goal is to isolate one or more cells secreting a particular protein or proteins of interest. This is accomplished using capture molecules and detection reagents specific for the protein or proteins of interest Again, the initial populations of cells to be analyzed can be primary cells or transformed cells into which constructs encoding different proteins have been introduced. Cells isolated by such methods can be subject to further analysis. For example, the recombinant construct occupying such cells can be sequenced to characterize the DNA coding sequence encoding the protein of interest.

3. Simultaneous Analysis of Multiple Markers

In some methods, multiple markers are detected on the same cell in a population. For example, one can detect the presence of two (or more) secreted proteins from the same cell, or one can detect the presence of one or more secreted proteins and one or more cell surface markers from the same cell. By such methods, one can develop a histogram of different cell types present in a population. The ability to characterize individual cells in this fashion provides useful information for analyzing differentiation patterns of cells and in clinical diagnostics. For example, certain diseases of the immune system are characterized by secretion of certain molecules from lymphocytes and/or expression of certain cell markers on the lymphocytes. Identification of cells secreting particular combinations of molecules and/or possessing certain cell markers serves to identify the immune disorder affecting the patient.

4. Diagnostic, Research and Therapeutic Methods

In some methods, cell populations are obtained from patients for diagnosis or monitoring the effectiveness of immunotherapy Such cell populations are often lymphocytes but can be obtained from tissues or body fluids, such as whole blood, semen, saliva, tears, urine, fecal material, sweat, buccal smears, skin hair, lymph nodes, tumors, and bone marrow samples. In some methods, cells are obtained from a patient for therapeutic purposes. In such methods, the goal is to identify a sub-population of cells having a desired property (e.g., secreting antibodies against a pathogen, secretion of a growth factor, cytokines or hormone, participation in a desired immune response). The desired cell type can be isolated, modified, stimulated, and or amplified and then reintroduced into a patient e.g., for immunotherapy.

Some examples in which isolation of particular populations of cells from a patient is suitable with a view toward in vitro growth and/or other manipulation are as follows:

Autoantigen-specific Th2 cells can be isolated from patients with cell-mediated autoimmune disorders (multiple sclerosis, diabetes, rheumatoid arthritis). Characteristic cytokine and cell surface markers for these cells are indicated below. The cells are propagated ex vivo and re-injected to augment remission or to prolong remission in the patient from whom they were obtained. Autologous antigen-specific cytotoxic T cells (CTLL) can be isolated from patients undergoing infection or suffering from cancer by expression of the CD8 cell surface marker. The CTLL's are specific for one or more antigens on the infecting microorganism or cancer. The CTLL's are amplified ex vivo to generate vaccines (e.g., anti-cancer, anti-intracellular bacterial infections (tuberculosis) or parasitic diseases (malaria, leishmania). In another application, cells from pancreatic islets of a patient are screened to identify those secreting insulin. These cells are amplified in vitro and re-introduced into the patient as a means of preventing or delaying Type 1 diabetes. The method can be performed during the prodromal period before clinical onset of disease in which some islet cells remain in the patient and are available for isolation and amplification. Alternatively, cells can be obtained from a healthy donor and transplanted to a diabetes patient with compatible HLA antigens and/or an immunosuppressive regime. In another method, cells from a patient with a genetic or other deficiency are screened to identify a subset of cells that have secretory defects for important bioactive molecules. These cells can be recognized from lack of signal when microdrops encapsulating the cells are contacted with a detection reagent specific for the bioactive molecule. A gene promoting secretion of the biomolecules under appropriate transcriptional control is inserted into the cells, the cells are amplified and re-injected into a patient. In another method, autologous multipotent stem cells are isolated from a patient, induced to differentiate in vitro to a desired lineage (e.g., heart, skin, nerve cells) and re-introduced to the patient to treat different disorders (e.g., myocardial infarction, skin burns, damaged nerves). Multipotent stem cells can be recognized by CD34 marker and/or lack of CD38, CD33, CD45RA and CD71.

5. Cytokine Assays

Cytokines play an important role in both the pathogenesis and treatment of disease. A number of these proteins have been approved for clinical use including: interferon-α, interferon-β, granulocyte-colony stimulating factor, and interleukin-2, and assessment of the functional status of T cells is essential for predicting patient response to therapy. Activation by mitogens or antigens, necessary for successful response to an immune system challenge, results in a cascade of cytokine secretion, receptor up-regulation, cellular proliferation and development of effector functions (7–12). Different cytokines are released from cells present in the immune system in response to signals from a variety of stimuli, including other cytokines. Mature T cells respond to antigen stimulation by producing unique combinations of these regulatory molecules and the functional consequence of these responses is dependent on cytokine secretion pattern (13–16). Cytokine secretion is widely used in both basic and clinical research as a crucial marker for cell differentiation and functional activity. The pattern of cytokine secretion combined with cell surface markers provides important information about the type, strength, and flexibility of a patient's immune response.

The present methods are particularly useful for detecting patterns of cytokine secretion, optionally in combination with cell surface markers, of individual cells. Applications include monitoring patient immune status before and after transplantation, determining antigen-specific response of T lymphocytes after vaccination, assessing effectiveness of treatments for cancers, autoimmune disorders, bacterial, and viral infections, such as AIDS (1–6), and determining immunotoxicity of drugs (7,8), and recovering single, viable T cells based on secretory profile combined with surface expression. Advantages of the present methods include: (1) high sensitivity (secreted cytokine levels of 1–10 ng/ml culture or 1.25–12.5 fg per microdrop are within the bounds of routine detection; (2) quantitative detection, (3) single cell analysis, (4) simultaneous detection of cytokines and cell surface markers; and (5) recovery of viable cells.

(a) Distinguishing Th1 and Th2 Cells

An exemplary diagnostic assay is the identification and recovery of Th1 and Th2 cell types. To identify and isolate Th1 or Th2 cells from heterogeneous populations, stimulated cells are encapsulated and cell surface antigen expression and cytokine secretion are simultaneously detected. Activated Th1 cells are identified as double-positive cells expressing CD3, CD4 (specific for helper cells) and CD69 (specific for activated cells) and secreting IFNγ, but not IL-4 (CD4$^+$CD69$^+$IFNγ$^+$IL-4$^-$ cells). Cells expressing a similar phenotype (CD3$^+$CD4$^+$CD69$^+$), but secreting IL-4, but not IFNγ (CD3$^+$CD4$^+$CD69$^+$IFNγIL-4$^+$ cells) are identified as Th2 cells. Multicolor flow cytometric analysis is performed using a combination of fluorochrome-labelled antibodies:: anti-CD4/Cy-Chrome (or CD4/ECD), anti-CD69/PC5, anti-IFNγ/FITC, and anti-IL-4/PE. Th1 and Th2 cells are optionally sorted by FACS and propagated. The ability to identify and isolate Th1 and Th2 sub-populations from mitogen or antigen stimulated peripheral blood mononuclear cells as quickly as possible is a useful for clinicians. These studies are used to: 1.) assess the immune status of patients, 2.) expand T cell clones to identify cells in autoimmune disease against in vitro targets, or 3.) create cytotoxic T cell clones that can be programmed to kill tumor cells in vitro, expanded, and used therapeutically in a donor. Using optimized stimulation conditions, both Th1 and Th2 cells can be stimulated so that the secretion of both IL-4 and IFNγ can be simultaneously detected within 48 hours on the same population of mononuclear cells.

(b) Analysis of Cytokine Secretion and Cell Surface Expression Profiles of Both Human Monocytes and CD34+ Cells After Activation with Different Stimuli Monocytes and dendritic cells are major sources of a variety of cytokines, including TNFα, IL-1α, IL-1β, IL-6, IL-8, and IFNγ (65,67,68). After stimulation with a range of antigens, these cells participate in both innate and adaptive responses. In blood, different subsets of circulating MNC (such as monocytes and B cells) can function as antigen presenting cells, communicating directly with T cells through specific and regulatory receptor ligand interactions and soluble cytokine interactions. Cytokines produced by this cell population play a key regulatory role in a number of clinical conditions. For example, increased production of the pro-inflammatory cytokines TNFα and IL-1 by monocytes has been implicated in septic shock (67,69,70). High local and systemic concentrations of cytokines released by monocytes have the potential to cause cascade effects on other cell types, including T cells, leading to pathological cytokine imbalances, which are characteristic of this condition (67,68,71). Measurement of cytokines produced by human monocytes in response to lipopolysaccharide (LPS) and other bacterial products is an in vitro model used to analyze events that occur in sepsis (72).

The present methods can be used to determine the response of single, viable monocytes to stimulus by identifying secreted cytokines and cell surface antigen expression. Examples of monocyte profiles of interest include: a) CD3/PC5, CD4/ECD, CD69/PE expression and TNFα/FITC secretion, and b) CD3/PC5, CD4/ECD, CD69/PE expression and IL-1β/FITC secretion.

(c) Analysis of in vitro Differentiation of CD34+ Human Cells Grown in Stromal-Free Liquid Suspension Culture Primitive cells of the hematopoietic system are characterized by their ability to generate large numbers of all known mature blood cell types. In peripheral blood, the majority of CD34$^+$ cells do not express CD38, CD33, CD45RA, and CD71 and, therefore, demonstrate CD34$^+$CD38$^-$CD33$^-$CD45RA$^-$CD71$^-$ phenotype. These cells differentiate in stages marked by the acquisition or loss of specific phenotypic characteristics and cytokine secretion (59,73,74). After differentiation, most CD34$^+$CD45RA$^+$CD71$^-$ cells are of granulopoietic lineage, whereas CD34$^+$CD45RA$^-$CD71$^+$ cells are of erythroid lineage. CD33 antigen is a characteristic marker for monocytes and myeloid progenitors, while CD38 is predominately expressed on T and B cells. The microdrop secretion assay can be used to monitor in vitro differentiation and proliferation of CD34$^+$ cells on an individual cell basis. Monitoring differentiation in this fashion allows culture conditions to be devised that direct differentiation along a desired path and/or which result in differentiation at a desired rate. Monitoring is also useful for defining culture conditions for ex vivo growth of human hematopoietic cells removed from a patient for subsequent reintroduction into the patient.

(d) Multiparameter Analysis

It is possible to attach several capture antibodies to the gel matrix and with cell surface markers for lymphocyte sub-populations and monocyte/macrophage/dendritic cell markers, a single mononuclear sample can be analyzed and sorted based on T lymphocyte sub-population (T helper or T cytotoxic), Th1 or Th2, natural killer, B cell, monocyte/macrophage, or dendritic cells. Using two capture antibodies for secretion and two cell-surface markers, using lymphocyte or monocyte gating, a single laser can be used to isolate lymphokine secreting lymphocyte or monocyte sub-population. With multiple tandem lasers a multi-parameter analysis can be obtained on the single mononuclear peripheral blood sample; multiple sort capabilities permits the isolation of each of the different lymphocyte and monocyte sub-populations.

6. Isolation of Rare IG Switch Variants

Antibody products are available for a variety of diseases, including cancer, heart and autoimmune diseases, and transplant rejection. Unfortunately, many of the hybridomas produced for both research and clinical use are of the IgM subclass, which are generally considered the least useful due to their pentameric structure and their lack of affinity for protein A and protein G. These make purification and modification of IgM antibodies difficult, and enzymatic digestion for Fab fragment production almost impossible.

Hybridomas spontaneously class-switch from producing IgMs to IgGs at a highly variable frequency depending on the cell line, but in general, switching frequencies of 1:10$^6$ are not uncommon (1,7) Many protocols have been devised to bias isotype production towards more favorable isotypes such as IgG1 or better still the IgG2 variants, but these procedures are lengthy and very labor-intensive involving multiple screening cycles. Some of these protocols include the use of different adjuvants or co-injection of stimulating factors or lymphokines, altering the dose of the antigen or boosting repeatedly (hyperimmunization) (1,4–6), yet prior methods remain unreliable due to the low frequency of switching relative to the number of cells that can reasonably be screened.

Use of microdrops, preferably conforming to the composition requirements described above provide a means for screening sufficiently large numbers of cells to isolate rare IgG isotype switch variants. Mixed populations of cells secreting antibodies of IgM isotype are propagated either in growth medium alone or in the presence of different B cell mutagens/stimulators (purified recombinant antigen, lypopolysacharides (LPS), retinoic acid) and/or cytokines (rmIL-4, rmIFNγ) for a period sufficient for isotype switching to occur in some cells (e.g., about seven days). Sometimes, to increase the rate of isotype switching, murine thymocyte feeder layers are also used.

The cell population is then encapsulated in microdrops. The microdrops can contain the same type of matrix shown in FIG. 1, preferably but not necessarily conforming to the preferred molar ratios of biotin to matrix molecules described above, and the capture molecule is an IgG isotype specific antibody. Typically, the capture molecule is an antibody. The capture molecule may be specific for all IgG subtypes or can be specific to a particular subtype, such as IgG1, IgG2, IgG2a, IgG3 and IgG4. In microdrops occupied by at least one cell secreting IgG isotype specific antibodies for capture reagent, the secreted antibodies are bound to the microdrops. In microdrops occupied by cell(s) secreting IgM isotype specific antibodies, secreted antibodies are not captured in the microdrops. After incubating the microdrops for sufficient time to allow antibody secretion e.g., 1–12 hr, a detection reagent is diffused into the microdrops. Typically, the detection reagent binds to the captured secreted antibody at a site different than the capture molecule. Typically, the detection reagent is an antibody against the captured secreted antibody of the IgG isotype of interest. Usually, the detection reagent is labelled, e.g., fluorescently, allowing detection of microdrops occupied by cells secreting IgG antibody. These microdrops can be sorted from other microdrops by FACS or other methods described above. Cells can then be recovered from the isolated microdrops. This selection method permits detection and isolation of sub-populations of cells secreting IgG as small as 0.0001%. In a variation of the above method, cells secreting antibodies are encapsulated under conditions such that most occupied microdrops are occupied by a plurality of cells. The analysis proceeds as before. If any one of the multiple cells encapsulated in each microdrop secretes an IgG antibody, then this microdrop is scored as positive. Cells recovered from such microdrops are then subjected to at least one further cycle of encapsulation and screening. Subsequent cycle(s) of encapsulation are performed with a lower mean ratio of cells per microdrop until, in a final round of screening, most occupied microdrops encapsulate a single cell. Such an iterative procedure allows larger populations of cells to be screened.

In a further variation, aliquots of cells can be dispensed into microtiter wells with up to about 1000 cells per well. Supernatant from the wells is then tested for antibodies of IgG isotype using a dipstick assay. Only cells from wells showing a positive signal by the dipstick assay are encapsulated and screened using the microdrop method.

7. Comparison of Microdrop Detection with Other Methods

A wide array of commercially available assay methods for identifying T cells of interest by both surface expression and secretory profiles are described below. Each approach has benefits for specific applications and several are easy to use, informative, and relatively inexpensive. The proposed microdrop format relies on use of microencapsulation technology, flow cytometry, and available antibody reagents. In contrast to other methods, the microdrop secretion assay makes it possible to detect small sub-populations of single cells secreting cytokines of interest, and to assay surface expression and secretory profile simultaneously. The technique is compatible with most ELISA type and flow cytometry assay procedures and also permits recovery of a population of functionally active cells for use in research and studies relating to immunotherapy.

Supernatant Assays for Detecting and Quantitating Cytokines Although several methods have been developed to quantify soluble cytokines in biological fluids and tissue culture supernatant, each technique has at least one significant limitation. Since these approaches are not single cell-based, they do not provide information on which cell subset secretes a cytokine of interest.

Bioassays Bioassays, which rely on growth of specialized cell lines in the presence of cytokines, are the least sensitive approach. Although relatively simple and well characterized, these formats are not reproducible and their low specificity frequently prevents cytokine differentiation between some cytokines (such as IL-α and IL-1β). Moreover, these assays are only semi-quantitative, and, in some cases, cytokine levels are underestimated due to the presence of inhibitors in biological samples (35).

ELISA Due to its inherent high specificity and sensitivity, the ELISA format is increasingly used to detect and quantitate soluble cytokines and chemokines, however, its use is limited to measuring a single cytokine per assay. Using enzyme-mediated signal amplification, the sandwich ELISA can measure physiologically relevant (i.e., >5–10 pg/ml) concentrations of specific cytokines or chemokines (36). The sensitivity of this approach has increased significantly with development of new approaches, such as the dissociation-enchanced lanthamide fluoroimmunoassay (DELFIA) using europium-labelled antibody (Ab) (37) and the cell culture-capture ELISA (2,38).

FlowMetrix™ System The FlowMetrix™ System (Luminex, Austin, Tex.) uses beads as the solid support for conventional immunoabsorbent assays with a green-fluorescent reporter dye followed by flow cytometric analysis. As the individual bead sets can be separated by flow cytometry, many assays can be performed simultaneously, permitting quantitation of multiple analytes in small (100–200 μl) volumes of cell culture supernatants or biological fluids (39). Because the FlowMetrix™ technology only measures the average secretion of the entire cell population, it is not useful for screening diverse cell populations with the aim of selecting and recovering a sub-population of viable cells. While the sensitivity of the FlowMetrix System is comparable to ELISA (picograms) for detecting single analytes, sensitivity drops to the nanogram level when performing multiplex analysis (39).

In situ Hybridization with Specific Cytokine Nucleic Acid Probes and Cytokine mRNA Expression Assays (RT-PCR) In situ hybridization or RT PCR are useful techniques for identifying cells expressing cytokine genes, although expression obviously does not indicate translation/secretion of the biologically active protein (40). Message Amplification Phenotyping (MAPPing) was also recently developed to assay and quantitate expression of specific cytokine messages in cells (41). MAPPing analysis utilizes a microprocedure for isolating RNA from cells followed by reverse transcription of total cellular RNA to cDNA and enzymatic amplification of cytokine-specific DNA fragments by PCR. This technique permits simultaneous determination of the collective pattern of mRNAs present in cells without the complexity and time required for individual cytokine assays, such as in situ hybridization. Simultaneous detection of a limited number of cytokines can also be performed using northern analysis or the ribonuclease protection assay (42). However, as with RT-PCR and in situ hybridization, these assays are not quantitative, are performed with killed cells, and do not directly measure secretion of native cytokine.

Single Cell Cytokine Assays Due to the importance of understanding the functional heterogeneity of lymphoid cells, interest in single cell assays has increased. Current methods include ELISPOT, limiting dilution analysis, reverse hemolytic plaque assays, immunohistochemistry, and single cell PCR (41,43). Although these methods permit analysis of cytokine secretion by individual cells, they are time consuming and labor intensive and are, therefore, not suitable for high throughput screening of large cell populations and recovery of single, viable, cells of interest after analysis is not possible.

Intracellular Cytokine Staining Recently, multiparameter flow cytometric analysis of individual cytokine producing cells within mixed cell populations has become useful for intracellular staining with specific anti-cytokine monoclonal Abs (3,6–8,11,44–48). High quality reagents and kits, as well as optimized protocols for simultaneous detection of cell surface and intracellular antigens (such as Becton Dickinson/PharMingen and R&D Systems) are commercially available. Prior to staining, cells are usually activated in vitro with various stimuli. The flow cytometric method is based on direct detection of intracellular cytokines and cell surface markers using fluorochrome-conjugated antibodies. Methods for cell preparation include: fixation, permeabilization. and disruption of cytokine secretion by treatment with drugs, such as monensin or brefeldin, in order to retain cytokines intracellularly. The ability to analyze key intracellular functional markers by multiparameter flow cytometry offers unique advantages for clinical studies. However, since assay procedures render cells non viable cells, measurement of functional secretion and recovery and propagation of cells of interest for research or therapeutic applications using FACS is not possible.

Affinity Matrix Technology Two new approaches for identifying and isolating cells based on specific protein secretion were recently developed Both use an artificial affinity matrix specific for the secreted product attached to the surface of viable cells. The first approach relies on biotinylation of cell surface proteins followed by incubation with streptavidin and biotinylated capture Ab. To prevent leakage of the secreted product, an incubation step is performed in pre-warmed, low permeability media containing gelatin. Fluorochrome-labelledantibodystaining is used for flow cytometric detection of positive cells (49,50). The second more direct approach, developed at Miltenyi Biotec (Auburn, Calif.), uses Ab-Ab conjugates directed against the common lymphocyte surface marker CD45 (49–54). After secretion, cells are labelled with fluorochrome-conjugated anti-cytokineantibody and then detected after incubating with magnetic microbeads coated with anti-fluorochromeantibody (anti-FITC or anti-PE Abs). Positive cells can be analyzed by flow cytometry before incubating with magnetic microbeads or enriched using a MACS column (52–54). Simultaneous staining for a cell surface marker (other than CD45, which is blocked by the Ab-Ab conjugate) is also possible.

Compared with other methods, the cellular affinity matrix technology permits analysis and sorting of large numbers of individual cells based on secreted products. Although successful isolation of viable cells has been reported, effects of the affinity matrix constructed on the cell surface on function and viability is a concern. Moreover, the amount of product secreted by individual cells, as well as the number of cell surface markers that can be simultaneously detected, are limited. In addition, it is difficult to estimate the secretion level. Using this assay format, the amount of secreted product bound to the affinity matrix will depend on the number of receptors expressed on the cell surface before labeling. A low concentration of binding sites within the affinity matrix will result in rapid saturation, making discrimination of low vs. high secretors nearly impossible.

A comparison of current cytokine detection methods is shown in Table 1.

TABLE 1

Comparison of assay characteristics for detecting cytokines

| Characteristics | Bioassays | ELISA | Bead-based system | RNA detection | ELISPOT | Intra-cellular cytokine staining | Affinity matrix technology | GMD assay format |
|---|---|---|---|---|---|---|---|---|
| Specificity | No | Yes | Yes | Yes | Yes | Yes | Yes | Yes |
| Detection Level | Low | 5–10 pg/ml | 0 pg/ml or 0–40 ng/ml | High | Moderate | Not determined | Not determined | –10 ng/ml or 25–12.5 fg/GMD |
| Quantitative | Semi-quantitative | Yes | Yes | No | No | No | No | Yes |
| Single Cell Analysis | No | No | No | possible | Yes | Yes | Yes | Yes |
| Simultaneous Cytokine and | No | NO | No | No | No | Yes | Yes, but only 1 | Yes |

TABLE 1-continued

Comparison of assay characteristics for detecting cytokines

| Characteristics | Bioassays | ELISA | Bead-based system | RNA detection | ELISPOT | Intra-cellular cytokine staining | Affinity matrix technology | GMD assay format |
|---|---|---|---|---|---|---|---|---|
| Cell Surface Marker Detection | | | | | | | secreted cytokine | |
| Viable Cell Detection | No | No | No | No | No | No | Yes | Yes |

8. Kits

The invention further describes kits for making microdrops. The kits contain matrix molecules (typically agarose) linked to biotin in a molar ratio of less than 0.85, preferably 0.01 to 0.2 moles biotin per mole matrix component molecules. The kit can also contain streptavidin, a capture molecule linked to second biotin molecules, and or a detection molecule. Kits also typically contain labeling providing directions for use of the kit. Kits are also provided for detecting IgG switch variants as described above. Such kits include biotinylated matrix molecules, preferably but not necessarily at the molar ratio described above, together with capture and detection molecules, and optionally labelling indicating instructions for use. The term labeling refers to any written or recorded material that is attached to, or otherwise accompanies a kit at any time during its manufacture, transport, sale or use. For example, the term labeling encompasses advertising leaflets and brochures, packaging materials, instructions, audio or video cassettes, computer discs, as well as writing imprinted directly on kits.

EXAMPLES

I. Materials and Methods

Cells and Culture Conditions

1) Transfected Cell Line We generated a stably transfected CHO cell line secreting hrIL-4 (CHO hrIL-4) using the liposome mediated procedure (Lipofectin®Reagent, Life Technologies) as follows: a plasmid containing the hrIL-4 gene was constructed by amplifying the gene sequence by PCR and inserting the sequence into the pIRESneo vector (Clontech). The pIRES vector contains an attenuated internal ribosome entry site (IRES) of the encephalomyocarditis virus (ECMV) which permits translation of two open reading frames from one messenger RNA. The transfection procedure and cloning were performed as recommended by the manufacturer. The CHO IL-4 cell line was maintained in MEM Alpha medium containing 5% dialyzed FBS and 1% penicillin/streptomycin by splitting trypsinized cells 1:10 twice a week.

2) Antigen-specific T Cell Line To generate an antigen-specific murine T cell line, Balb/c female mice were immunized with a synthetic peptide M1081 (a kind gift of N. Rosenthal, Mass. General Hospital, Boston, Mass., sequence: CGMYCAYTIPGMGGNSLM, MW 1869). We coupled this peptide, which is a portion of E ITF2A, a protein involved in cardiac development, to KLH, used as a carrier, and animals were injected intraperitoneally every 4 weeks for one year. To make a single cell suspension from aseptically removed spleen and mesenteric lymph nodes, organs were desegregated on a 70 μm cell strainer in a petrii dish using a syringe plunger. Then the single cell suspension was resuspended in DMEM (GibcoBRL, Grand Island, N.Y.) containing 10% fetal bovine serum (FBS, HyClone, Logan, Utah), HEPES, antibiotics (penicillin and streptomycin, GibcoBRL), and $5 \times 10^{-5}$ M of 2-mercaptoethanol (2-ME, Sigma, St. Louis, Mo.). To lyse erythrocytes, the cell suspension was treated with lysis buffer (Sigma) and washed 2 times with Hanks balanced salt solution (HBSS, Gibco) containing 5% FBS. Cell viability and count were performed in a hemocytometer chamber using a Trypan Blue (TB, Sigma) exclusion assay. Aliquots of splenocytes were frozen (−70° C.) for use as autologous feeder cells. According to the conventional procedure described by Londei, M., et al., 1991 (55), an antigen specific T cell line was generated using mLN cells and maintained in culture by re-stimulating with alternative weekly cycles of specific Ag in the presence of mitomycin C treated autologous feeder cells and mrIL-2.

3) Mouse Splenocytes Spleens were aseptically removed from naïve Balb/c female mice and a single cell suspension was prepared, as described above. The cell concentration was adjusted to $1.5 \times 10^6$/ml in complete medium and 2 ml ($3 \times 10^6$ cells) was then added to each of three wells of the 24-well plate. The remaining cells were aliquoted and frozen. To stimulate cells, we added either ConA (5 μg/ml) or PHA (5 μl/ml) to experimental wells and mixed by pipetting. Cells in complete medium alone were used as a negative control. The plate was incubated at 37° C. in 5% $CO_2$ for 24 hr prior to performing the microdrop cytokine secretion assay.

4) Fresh human PBMCs were isolated from a healthy donor using the Histopaque 1077-I (Sigma) technique. Isolated cells ($3 \times 10^6$/ml) were cultured in RPMI-1640+10% FBS (dialyzed) in the presence or absence of PHA (5 μg/ml) for 24 hr at 37° C. in 5% $CO_2$.

Immunoreagents For use as capture and reporter antibodies in the microdrop secretion assay format, biotinylated and fluorochrome-labelled (FITC or PE) monoclonal antibodies against mouse cytokines and purified recombinant cytokines (mrIFNγ, mrIL-2, mrIL-4, mrIL-6), PE-labelled anti-mouse CD3, and antibodydirected against FcγII/III receptor (Fc Block™) were obtained from PharMingen, Inc. (San Diego, Calif.). The hrIL-4 antibody pair was also obtained from PharMingen. Mitomycin C, ConA, and PHA were obtained from Sigma (St. Louis, Mo.). Anti-human CD3/PE-Cy5 and CD4/ECD Abs were obtained from Immunotech (Beckman Coulter, Miami, Fla.). Anti-human CD69/FITC, anti-human IFNγ/PE, biotinylated anti-human IFNγ, and purified rhIFNγ were obtained from BD/PharMingen (San Diego, Calif.).

Gel Microdrop Formation Two biotinylated agarose encapsulation matrices, CelBioGel™-1 or CelBioGel™-2, which contain different amounts of biotin and CelMix™ 200 emulsion matrix (One Cell Systems, Inc., Cambridge, Mass.) were used to prepare microdrops. To prepare a batch of 20×10⁶ microdrops, one 400 μl aliquot of agarose was heated in a microwave for 75 seconds, and 25 μl of 10% pluronic acid (Sigma) was added as a surfactant. To make unoccupied microdrops for use in generating titration curves, 100 μl of complete medium was added to the agarose/surfactant mixture. After vortexing and equilibrating at 37° C. for 3 min, the mixture was added dropwise to 15 ml of CelMix™ 200 emulsion matrix pre-warmed to 37° C. in a glass scintillation vial. The vial was attached to the CellSys™ 100 Microdrop Maker (One Cell Systems, Inc.) and the mixture was emulsified as follows: 2,100 rpm for 1 min at room temperature (RT), 2,100 rpm for 1 min in an ice bath, at 1,100 rpm for 10 min in an ice bath. The oil was removed by centrifuging at 650 g for 10 min and then washed twice with 10 ml of HBSS by centrifuging at 450 g for 5 min.

Single Cell Encapsulation After counting in a hemocytometer chamber and determining viability using a Trypan Blue exclusion assay, cells from actively growing cultures were resuspended in complete medium at a concentration of 1×10⁷/ml. To make conditioned medium, cell culture supernatants were centrifuged (800 g for 5 min) to remove cell debris. Then, 1×10⁶ cells in 100 μl of complete medium were added to the agarose/surfactant mixture and microdrops were formed as described above. To increase the number of occupied microdrops, in some experiments two aliquots of CelBioGel™-2, each containing 1×10⁶ cells, were resuspended in 15 ml of CelMix™ prior to the encapsulation procedure described above.

Multiple Cell Encapsulation Prior to encapsulation, cells are grown in two 75 cm flasks or in two 12-well plates (2 ml/well) for 5 days. Pooled cells (total number is higher than 2×10⁶) are counted and resuspended in 200 or 300 μl of growth medium. Two aliquots of 500 μl melted CelBioGel are vortexed with 25 μl of 10% Pluronic F-68 solution (Sigma-Aldrich), equilibrated at 37° C. for 3 min and then each is mixed with 100–150 μl of cell suspension. These mixtures are added to 15 ml prewarmed CelMix™, covered and shaken vigorously 10 times to form an emulsion. Then the vial is attached to a CellSys100™ Microdrop Maker (One Cell Systems, Inc). To generate large diameter microdrops, 1800 rpm and 1000 rpm speeds are used for emulsification. The generated microdrops are washed two times in DPBS to remove oil, filtered through a 70 μm cell strainer and counted in a hemocytometer chamber.

Immobilization of Capture Antibody in Agarose Matrix microdrops were then washed with HBSS+2% FBS and a bridge was constructed by incubating the suspension with streptavidin (10 μg/ml) in 8 ml of DMEM+5% FBS for 15 min at RT. After washing with HBSS+2% FBS, microdrops were resuspended in 4 ml of DMEM+5% FBS and the same volume of capture reagent (biotinylated anti-cytokineantibody at 10 μg/ml) was added to make a 5 μg/ml final concentration. The sample was then incubated for 15 min at RT. The microdrop suspension was washed again with HBSS+2% FBS to remove unbound capture antibody.

Cytokine Secretion Incubation and Fluorescent Labeling Encapsulated cells were then resuspended in 30 ml of pre-warmed (37° C.) complete medium and incubated at 37° C. in 5% $CO_2$ for either 3.5 hr or 18 hr to permit cytokine secretion. After the secretion incubation, the microdrop suspension was washed with HBSS+2% FBS and then resuspended in 4 ml of DMEM+5% FBS. The same volume of DMEM+5% FBS containing fluorochrome-conjugated anti-cytokineantibody(10 μg/ml) was added to the microdrop suspension. In order to discriminate dead cells, propidium iodide (PI, Molecular Probes, Eugene, Oreg.) at a final concentration of 2 μg/ml was added. After incubating for 20 min at RT, the sample was washed and transferred to special tubes for flow cytometric analysis.

Cell Surface Staining After labeling the secreted cytokine with reporter Ab, CD3 cell surface receptors were stained with PE labelled anti-CD3 monoclonal Ab. To reduce non-specific immunofluorescent staining mediated by Fc receptors, encapsulated cells were resuspended in 1 ml of HBSS+2% FBS and incubated with 1 μg Fc Block™ for 15 min at 4° C. The sample was then washed and stained with anti-CD3 monoclonalantibodylabelled with PE by incubating in 1 ml of HBSS+2% FBS containing 5 μg of anti-CD3/PEantibodyfor 30 min at 4° C. After washing with HBSS+2% FBS, the sample was analyzed by flow cytometry.

Assay Controls In addition to the secretion sample stained with fluorescent Ab, four separate assay controls were prepared: a) Unstained control (to detect cell autofluorescence): an aliquot of microdrops was saved directly after cell encapsulation. b) No capture control (to detect background fluorescence due to non-specific binding of immunoreagents to the agarose matrix or the cell surface): an aliquot of microdrops was processed as normal, except the capture Ab-binding step was omitted. c) Positive control (to ensure that reagents worked properly): an aliquot of microdrops was removed after loading with capture antibody prior to the secretion incubation, incubated with purified cytokine, and d) Isotypecontrols to determine ifnonspecific binding of fluorescently-labelled detection antibodies occurres an aliquot of microdrops was removed after the secretion incubation step and incubated with a similarly labelled related isotype control antibody labelledas the detection antibody.):

Microdrop Supernatant Assay As an alternative to conventional ELISA, we also developed a cell based microdrop supernatant secretion assay (analogous to the Flowmetrix™ (Luminex, Austin, Tex.) system) to assess the detection levels derived from the cytokine titration curves. An aliquot of microdrop suspension from the secretion assay protocol was processed as the positive control (described above) except it was incubated with culture supernatant (directly or after diluting with fresh medium at a ratio of 1:10 or 1:100) instead of with purified cytokine. Extrapolating from the titration curve generated with cell free microdrops, the relative cytokine concentration in the supernatant was determined according to the mean fluorescence intensity and supernatant dilution factor. This assay format was used to measure cytokine concentration in cell culture supernatants collected the same day the secretion assay was performed.

Impact of Microdrop Size on Assay Reproducibility Microdrops are generated using an emulsion process which results in a Gaussian size distribution; the majority (~76%) of microspheres fall within one standard deviation on either side of the mean. Among occupied microdrops, the size distribution is smaller, since smaller microdrops tend to be unoccupied. For the cytokine secretion assay, reproducibility is less dependent on the size variation of the microspheres than on the number of capture sites per microdrop and the amount of cytokine secreted by individual cells during the secretion time.

Potential for Assay Crosstalk "Crosstalk" (leakage of the secreted product from microdrops occupied by secretors) could result in false-positive microdrops and can be assessed using the supernatant assay. This is a concern for conditions during which cells (such as hybridomas or transfected cells) secrete protein in excess of capture antibody bound to the matrix. Crosstalk can be virtually eliminated by choosing the appropriate secretion time. For example, when performing the microdrop secretion assay to isolate high protein secreting CHO and hybridoma cells for bioprocessing applications, as soon as signal exceeds background, frequently in 15–30 minutes and prior to saturation of the antibody binding sites, then cells can be sorted. For conditions present for assaying sub-populations of cytokine secreting cells, since cytokine levels are ordinarily low, and below the capture capacity of an average microdrop, "crosstalk" remains a theoretical concern. Quantitative analysis of secretion and inter-experiment comparisons can also be performed to ensure that the number of capture sites is in excess of the amount of secreted cytokine.

Microscopy Encapsulated cells were visualized using a Nikon ECLIPSE E600 epifluorescence microscope equipped with a phase contrast objective. Cell viability after Trypan Blue staining was evaluated microscopically. Prior to flow cytometric analysis, a 480/30 nm excitation and a 535/40 nm barrier filter set was used to examine microdrops stained with FITC. Red fluorescence from PI-treated cells as well as PE staining was detected by examining samples using 546/10 nm excitation and a 590 nm barrier filter. Samples were observed using either 400× or 1000× magnification. Fluorescence microscopy was used to determine the viability of encapsulated cells and to identify positively stained microdrops containing secretors. Low background fluorescence in no capture control and strong fluorescence in positive controls indicated that the assay was performed properly.

Density Gradient Separation

Separation of the unoccupied from occupied microdrops is achieved by centrifugation of microdrops through a stepwise density gradient, for example 5, 6, 7 and 8% Percoll (Sigma #P1644) in DPBS. A gradient consisting of 1.5 ml of each of the four concentrations is aseptically prepared in a 10 cc syringe (B-D) with a luer lock tip and a nylon stopcock. A 2 ml microdrop suspension is layered on the top of the gradient and a piece of Parafilm is placed over the top. The syringe assembly is placed in a 50 ml centrifuge tube (Corning) and the assembly is centrifuged at 400×g for 20 minutes at 18–22° C. The layer of 6% Percoll contains the unoccupied microdrops and is discarded. Collection of the bottom 3 ml, 7–8% Percoll, results in recovery of primarily (~90%) cell-occupied microdrops. Percoll is removed by washing the microdrops in two volumes of buffer, twice and centrifuging at 400×g.

Flow Cytometry Microdrop samples were analyzed using a FACScan (Becton Dickinson, San Jose, Calif.) or an EPICS Elite™ (Beckman Coulter, Miami, Fla.), both available at One Cell Systems. Fluorochrome-labelled (FITC or PE) detection reagents and PI-labelled dead cells were excited by the 488 nm spectral line of an argon laser. Green (FITC) and red (PE or PI) fluorescence were collected using 525 nm, 575 nm, and 630 nm long pass band filters, respectively. For statistical analysis, EPICS Elite 4.02 software (Beckman Coulter) was used. To measure the fluorescence intensity of unoccupied microdrops (titration curves), 20,000 events were acquired for each sample. Occupied microdrops have increased light scatter characteristics compared with unoccupied microdrops and were distinguished in a plot of forward and right angle light scatter. Using light scatter, occupied microdrops were easily resolved from unoccupied microdrops, which were eliminated from the data acquisition by increasing the forward scatter threshold or discriminator until unoccupied microdrops disappeared from the screen. Microdrops occupied by two or more cells were distinguished from microdrops occupied by single cells by increased FS. Only microdrops occupied by single viable (PI negative) cells were gated for data acquisition and analysis. To identify this sub-population, dual parameter dot plots (PI vs. FS) were used. This microdrop sub-population was then analyzed for green (FITC) or red (PE) fluorescence in both control and secretion samples. Fluorescence higher than the negative control represented cytokine secreting cells. For compensation settings, samples stained with only FITC or PE-labelled detection reagents or PI were run and the spectral overlap in each sample was electronically subtracted. Samples were run at a rate of approximately 600 events per second and at least 10,000 gated events were collected.

Fluorescence Activated Cell Sorting (FACS) We sorted cytokine secreting cells using an EPICS Elite™ equipped with a 100 μm nozzle. Fluorescence of the sub-population of microdrops occupied by single PI negative (viable) cells was analyzed. Microdrops generating positive fluorescence were gated and sorted at a rate of 600–800 events per second. Positive events were collected in a 15 ml tube filled with growth medium containing 25% of conditioned medium.

Recovery and Propagation of Viable Cells After Sorting Positive microdrops collected during the sorting procedure were placed in growth medium containing 25% of conditioned medium and 1 U/ml (for transfected CHO cells) or 3 U/ml of agarase (New England Biolabs, Beverly, Mass.) and then incubated at 37° C. in 5% $CO_2$ for 7–10 days. To recover antigen-specific lymphocytes after an 18 hr incubation in the presence of agarase (3 U/ml) and mrIL-2 (10 ng/ml), specific Ag (10 μg/ml), mrIL-2 (10 ng/ml) and mitomycin C treated autologous feeder cells, diluted in a 1:1 ratio with sorted cells, were added and the flask was returned to the incubator. Cell viability and growth were evaluated every other day using microscopy after Trypan Blue staining and counting in a hemocytometer chamber.

Attachment of Microdrops to a Plastic or Glass Surface

Attachment of microdrops to a sterile, uncoated polystyrene surface (B-D Falcon Petri dish, #351008 or 1006) is achieved by preparing microdrops from agarose to which biotin is covalently attached (e.g. CelBioGel™-1). The microdrops are prepared according to the protocol that results in the majority of cell-containing microdrops occupied by single-cells. The occupied microdrops obtained from the Percoll gradient are washed twice in protein-free tissue culture buffer, Dulbecco's phosphate buffered saline (DPBS) or Hank's balanced salt solution (HBSS). Microdrops are added to a Petri dish containing buffer and allowed to remain undisturbed on a level surface at room temperature. Attachment is complete within 15 minutes and is believed to be the result of bonding of the agarose surface to functional groups of the polystyrene, probably via hydrogen bonding, and is blocked only if protein is present in the buffer during the attachment step. The blocking of sites on the Petri dish to which there are no microdrops attached is achieved by adding serum, such as 5% fetal bovine serum. Blocking is complete within 5 minutes and insures that the solid phase network is constructed only in the microdrop and not on the plate surface. The protein, media and incubation conditions of all subsequent steps do not interfere with or reverse attachment.

Cells and Culture Conditions for Antibody Secretion Hybridoma cell line CRL-8018 secreting $mIgM_κ$ specific for hepatitis B virus surface antigen (HBsAg) and TIB-114 secreting mIgG3 specific for sheep red blood cells (both from ATCC) were used in experiments. CRL-8018 hybridoma cells were grown in Iscove's modified Dulbecco's medium supplemented with 20% FBS (Gibco Lab.). DMEM supplemented with 10% FBS (Gibco BRL Products was used for the TIB-114 hybridoma cell line. Both hybridoma media also contained 2 mM L-Glutamine (Life Technologies) and Pen/Strep (Penicillin 1 U/ml/ Streptomycin 1 µg/ml, Life Technologies). Cultures were maintained in at 37° C., 5%$CO_2$ in a humidified incubator at densities between $1\times10^5$ to $1\times10^6$ cells/ml by addition or replacement of fresh medium twice a week.

Microdrop Isotype-Specific Detection and Isolation Assay Artificial mixtures of mouse IgM secreting hybridoma CRL-8018 and mouse IgG3 secreting hybridoma TIB-114 were used in experiments. First, CRL-8018 cells were grown for 7 days in TIB-14 growth medium (DMEM+10% FBS) and mIgM secretion level was determined by testing supernates using IsoStrip™ (Roche DiagnosticsCorp.). CRL-8018 cells were then spiked with TIB-114 cells at 0.1%, 0.01%, or 0.001% and microdrop-based enrichment was performed after encapsulating $2\times10^6$, $25\times10^6$ or $50\times10^6$ cells. All microdrops containing at least one IgG secreting cell were sorted, as described below, pooled, and cultured for 5 days at 37° C. and 5% $CO_2$ in DMEM+10% FBS suppelemented with 5 U/ml of agarase Induction of Class-Switching Using CRL-8018 cell line, we investigated and evaluated methods of increasing the number class-switching events in-vitro. Cells were plated in 75 cm² flasks or in 12-well plates at $1\times10^4$/ml and incubated for 7 days in complete growth medium supplemented with:

recombinant HBsAg (1 µg/ml) plus rhIL-4 (10 ng/ml);
recombinant HBsAg (1 µg/ml) plus rmIFNγ (10 ng/ml);
LPS (1 µg/ml) plus rmIL-4 (10 ng/ml);
LPS (1 µg/ml) plus rmIFNγ (10 ng/ml);
retinoic acid at 25 nM, 50 nM, or 100 nM.

After incubating for 7 days, culture supernates were tested for the presence of IgM and/or IgG production using IsoStrip™ according to the manufacturer's instruction.

Determination of in-vitro Induced Switching Rate Using Sequential Sublining CRL-8018 cells were resuspended in growth medium supplemented with mitogen(s)/growth factors as described above and plated out in ten 96-well plates at a density of 1,000 cells/well. Cells were cultured at 37° C., 5%$CO_2$ in a humid incubator for 5 days. Cell culture supernates were collected and an isotype-specific ELISA performed. Briefly, 96-well flexible assay plates, previously coated with 10 µg/plate of purified goat anti-mouse IgG (Jackson Immunochemicals) in 20 mM $NaHCO_3$ (Sigma-Aldrich), 50 µl/well, were incubated overnight at 4° C. and then washed 3 times in Dulbecco's phosphate buffered saline without calcium and magnesium/0.2% Tween 20 (DPBS-/Tween) (Sigma-Aldrich). Non-specific protein binding sites were blocked using PBS+1% BSA, 200 µl/well for 2 hr at room temperature (RT).

100 µl of each of the culture supernates were harvested and incubated in the anti-IgG coated plates for 2 hr at RT. The assay plates were washed three times in DPBS-/Tween, and 50 µl of HRP conjugated goat anti-mouse IgG (Jackson Immunochemicals) diluted 1:100 in PBS/Tween were applied to each well and incubated at RT for 1 hr. Plates were washed again and developed using 100 µl of TMB substrate solution (Sigma-Aldrich). The reaction was halted with 0.5M $H_2SO_4$ (Sigma-Aldrich) and plates were read at 405 nm on an $EL_x800$ ELISA plate reader (Bio-TEK Instruments, Inc.). Five rounds of the above procedure were performed to determine the switching rate.

Determination of Spontaneous and in-vitro Stimulated Switching Rate Using the Microdrop Isotype Capture and Isolation Assay Due to the low rate of isotype switching, analysis of large cell populations is necessary. -We, therefore, used a modified microdrop encapsulation protocol to isolate spontaneous or in-vitro induced rare IgG isotype switch variants among IgM secreting hybridoma cells. If the IgG concentration in supernatants was <0.1 µg/ml, we initially encapsulated multiple cells, followed by single cell encapsulation. In all cases, if,after in-vitro induction, the concentration of secreted IgG in supernatants was >0.1 µg/ml, one round of single cell encapsulation was sufficient- for discriminating and sorting a small sub-population of positive cells.

Two aliquots of 500 µl melted CelBioGel-3™ were vortexed with 25 µl of 10% Pluronic F-68 solution (Sigma-Aldrich), equilibrated at 37° C. for 3 min and then each was mixed with at least $2\times10^6$ hybridoma cells in 100–200 µl of growth medium. These mixtures were added to 15 ml prewarmed CelMix™, covered and shaken vigorously 10 times to form an emulsion. Then the vialwas attached to CellSys100™ Microdrop Maker (One Cell Systems, Inc) and the emulsion was mixed at 1800 rpm for 1 min at RT, then 1800 rpm for 1 min at 0° C., and subsequently 1000 rpm for 6 min at 0° C. Microdrops were washed three times in DPBS to remove oil and then incubated in 7 ml DPBS containing streptavidin (Sigma-Aldrich) at a final concentration of 10 µg/ml for 10 min at RT.

After incubating with streptavidin, microdrops were washed three times by resuspending in 15 ml DPBS-followed by centrifugation at 1500 rpm for 5 min and then incubated with 10 µg/ml of biotinylated goat anti-mouse IgG for 10 min. Microdrops were again washed three times in DPBS-(as above) and resuspended in 20 ml of prewarmed growth medium and incubated at 37° C. for 2 hr for antibody secretion by the encapsulated cells. After incubation, microdrops were pelleted by centrifugation at 1500 rpm for 5 min, resuspended in cold DPBS- and labelled with 10 µg/ml of FITC-conjugated goat anti-mouse IgG-specific antibody (Jackson Immunochemicals). microdrops were washed twice in HBSS, resuspended in 2 ml of growth medium and sorted using a Coulter EPICS Elite; gating was set to sort only highlypositive microdrops, based on controls.

To determine spontaneous and in-vitro induced switching rate using the microdrop isotype capture and isolation assay, CRL-8018 hybridoma cells were plated out in two 75 cm² flasks or two 12-well plates (2 ml/well) at a density of $1\times10^4$ cells/ml in complete growth medium alone or in the presence of stimulators as described above. Cells were cultured at 37° C., 5%$CO_2$ in a humid incubator for 5 days. Cell culture supernates were harvested and IgM and/or IgG production was tested using IsoStip™ or an ELISA-based mouse Isotyping kit (Zymed, Inc.). All cells from 75 cm2 flasks and from wells positive for IgG production were pooled, resuspended in 100–200 µl of growth medium and encapsulated in microdrops. The first round of isotype capture and isolation enrichment with multiple occupied microdrops was then performed, as described above. After sorted cells were propagated in culture for 5 days, the second round of the assay was performed usingmicrodrops occupied by single cells. After isolation by FACS, IgG secretors were plated out in 96-well plates, 1 cell/well. The number of recovered clones was estimated using supernatant ELISA after incubating plates at 37° C. in 5%$CO_2$ for 14 days.

Generation of Controls for the Microdrop Isotype Capture and Isolation Assay Unstained control was used to measure autofluorescence of encapsulated cells. For each experiment, the negative (no capture or NOC) control was generated by omitting incubation of one aliquot of microdrop suspension with capture (biotinylated) anti-IgG. As a positive control, one aliquot of microdrop suspension was incubated with purified mouse IgG (Sigma) at a final concentration of 1 µg/ml followed by staining with detection Ab.

Fluorescence Activated Cell Sorting Cell sorting was performed using an EPICS Elite™ Coulter Corp. with a 100 µm flow nozzle. FITC-labelled detection regents were excited by the 488 nm spectral line of an argon laser. Green (FITC) fluorescence was collected using a 525 nm, long pass band filter. For statistical analysis, EPICS Elite 4.02 software was used. First, occupied microdrops were distinguished from unoccupied micodrops by increasing forward and right angle light scatter. The light scatter properties of occupied microdrops were easily resolved from unoccupied microdrops, which were eliminated from the data acquisition by increasing the forward scatter threshold or discriminator until they no longer appear on the screen. To enrich for IgG switched variants during the first step of the procedure, all occupied microdrops were acquired and those which had at least one positive cell were sorted and pooled for culturing. For the second step of enrichment, single occupied microdrops were discriminated from multiple occupied microdrops using their different forward scatter characteristics, gated and only single occupied microdrops containing positive IgG switched cells were gated for sorting. Samples were run at a rate of approximately 600 events per second with 50,000 or more gated events collected. Dead cells have increased side scatter and low forward scatter, and, therefore, this sub-population can be gated out. Singly occupied microdrops were gated and analyzed for green fluorescence both in control and secretion samples. FITC fluorescence higher than the negative control represented antibody-secreting cells. The sub-population of the brightest occupied microdrops was gated and sorted at a rate of at least $10^6$ microdrops per hour. Up to approximately 50,000 events were collected.

Cell Recovery and Propagation After Microdrop Encapsulation and Sorting Microdrops sorted after the first step of enrichment were pooled in 1 ml of growth medium for incubating in one well of a 12-well plate. After the second round of the enrichment process, the concentration of sorted single occupied microdrops was adjusted to 10 cells/ml by resuspending in growth medium and cells were deposited in 96-well plate(s) (one cell per 100 µl per well). To release cells frommicrodrops, 5 U/ml of agarase (New England Biolabs, Inc.) was added to the medium. This routine procedure did not affect cell viability. After incubating overnight at 37° C. and 5% $CO_2$, 1 ml or 100 µl of fresh medium were added to each well and incubation was continued until visible cell growth was detected. ELISAs were performed with supernatants on all proliferating hybridoma clones and those producing the highest amounts of antibody were selected and propagated in 15-ml culture flasks.

Results

1. Determination of Ratio of Biotin to Agarose

The ratio of biotin to agarose can be determined by NMR by combining a known weight of biotinylated agarose with a known mass of a standard that gives a recognizable NMR pattern. NMR service is commercially available (e.g., NMR Analysis and Consulting, Decatur, Ill.). Potassium hydrogen phthlatate (KHP) is suitable as a standard. The frequencies of the NMR spectrum are expressed on a ppm scale. The intensities of signals are proportional to the number of H atoms emitting signals. The KHP signal can be integrated over a range of 7.7 to 7.9 ppm. Biotin generates many NMR signals. A signal at 2.40 ppm that comes from two hydrogens next to the carboxyl group is suitable for analysis. The percentage mass of biotin present in the biotinylated agarose can be determined from the following formula $$A_{biotin}/A_{KHP} \times 4/2 \times 244.3/204.2 \times wt_{KHP}/wt_{sample} \times 100.$$

A stands for the areas of NMR peaks, 4 is the number of H's giving rise to the KHP peak, 2 is the number of H's in the biotin peak, 244.3 is the molecular weight of biotin and 204 the molecular weight of KSP. The percentages by weight can be converted to molar percentages by dividing the relative masses by the respective molecular weights of 244.3 for biotin and 120,000 for agarose. For example, CelBioGel-1 showed a mass ratio of 1 g agarose to 0.00225 g biotin, corresponding to a molar ratio of 0.92 mmoles biotin to 0.83 mmoles agarose or 1.1 moles biotin per mole agarose.

Alternatively, the ratio of biotin to agarose can be determined using an ImmunoPureHABA kit (Pierce). The kit detects biotin by displacing avidin from a complex formed with HABA (2-[4'hydroxyazobenze) benzoic acid). Displacement causes a decrease in absorbance of HAB-avidin solution measured at 500 nm, which is proportional to the concentration of biotin.

The kit was used to determine absorbance on CelBioGel-1. Absorbance of HABA-avidin solution (0.9 ml) was 0.924. Absorbance of HABA-avidin after adding 0.1 ml of CelBioGel (10 mg/ml) was 0.532. The amount of biotin in the CelBioGe was calculated using the formula (described by Pierce)

1.) D A500=(0.9×0.924)−0.532=0.299

2.) mmoles of biotinylated agarose/ml=10/120000=8.33× 10-5

3.) µmoles of biotin/ml reaction mixture=DA500/ absorption coefficient=0.299/34=8.8×10-3

4.) moles of biotin/mole of biotinylated agarose=8.8×10-3×(10)×(1):8.33×10-5×1000 (µmoles/mmole)=1.056

This is within a 5% margin of error of the value determined by NMR.

2. Comparison of Biotinylated Matrixes

This example compares three types of biotinylated agarose termed CelBioGel™-1,-2, and -3 having molar ratios of a biotin to agarose of 1:1, 0.2:1, and 0.04:1 within a +/−10% experimental error margin. To determine assay sensitivity and to assess optimal concentrations of biotinylated capture and fluorochrome-labelled reporter antibody, cell free microdrops were incubated in serial dilutions of mrIL-4, mrIL-6, mrIFN□, and hrIL-4 using either CelBioGe-1 or CelBioGe-2 for 15 min on a rotator at RT with 10 µg/ml of streptavidin (Sigma) in 4 ml of DMEM with 2% EBS and the secretion assay was performed as described above, except no cells were added. Excess streptavidin was removed by washing with HBSS plus 2% FBS (used for all washes). The unoccupied microdrop preparation was then incubated with biotinylated capture antibody (5 µg/ml) in 4 ml of medium for 15 mm on a rotator at RT, followed by washing to remove unbound reagent. Aliquots of this preparation (8×105 microdrops) were incubated with varying dilutions of purified cytokine (100 ng/ml to 1 ng/ml) and incubated at 37° C. for 30 minutes on a rotator. Unoccupied microdrops incubated in HBSS plus 2% FBS served as the negative control. Following the washing procedure, all samples were incubated with fluorochrome-conjugated reporter antibody (5 µg/ml) for 15 min on a rotator at RT, washed, and transferred into different tubes for single color flow cytometric analysis. Mean fluorescence intensity is proportional to the cytokine concentration captured in single microdrops.

Figure 2:
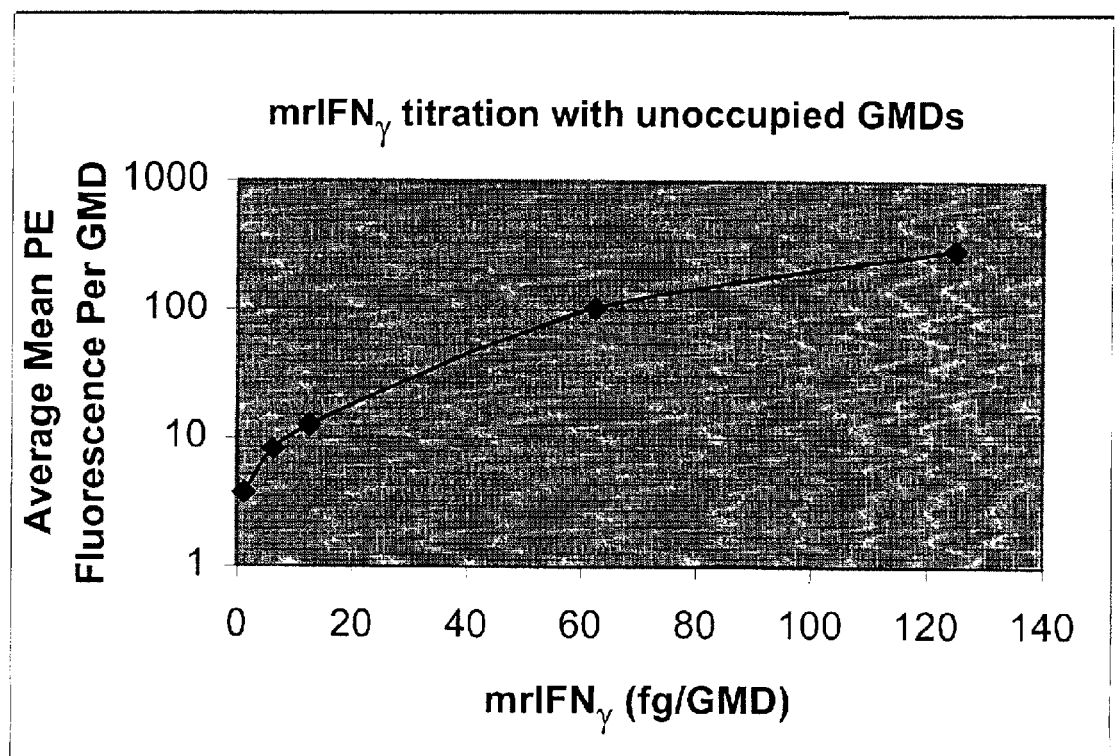
FIG. 2. mrIFNγ titration curve generated using unoccupied GMDs. Unoccupied GMDs were prepared from CelBioGel-™-2. After treating with streptavidin and biotinylated anti-IFNγ Ab, GMDs were incubated with decreasing concentrations of mrIFNγ. After labeling with PE-conjugated anti-IFNγ Ab, the cytokine bound to the agarose matrix was detected by fluorescence.
Figure 3A:
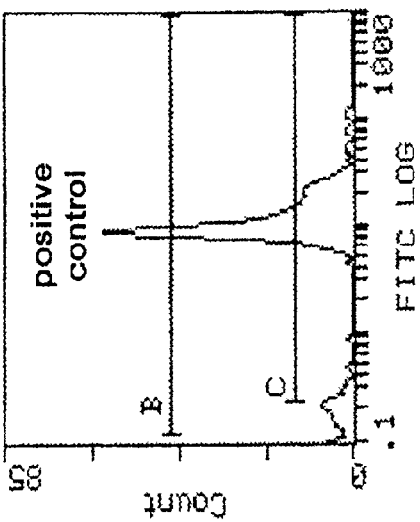
FIG. 3. GMD cytokine secretion assay using CHO cells transfected with hrIL-4. The GMD secretion assay was performed using a 1 hr secretion incubation. Flow cytometry histograms 1,2 and 3 represent the unstained, negative (or "no capture"), and positive controls, respectively. GMDs occupied by single cells were gated (histogram 4, gate A). Viable (PI negative) cells were chosen for data acquisition (histogram 4, gate B) and analyzed for FITC fluorescence (histogram 5). Positive events were identified under marker C (histogram 6).
Figure 3B:
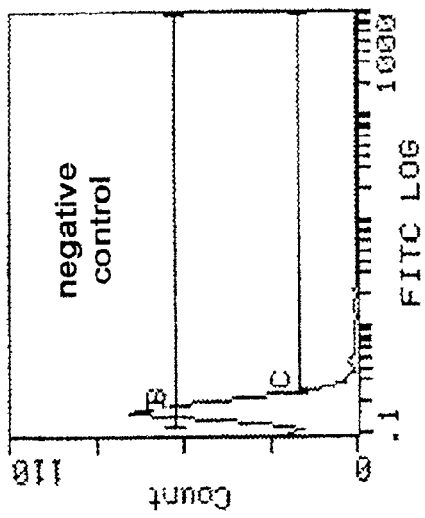
Figure 3C:
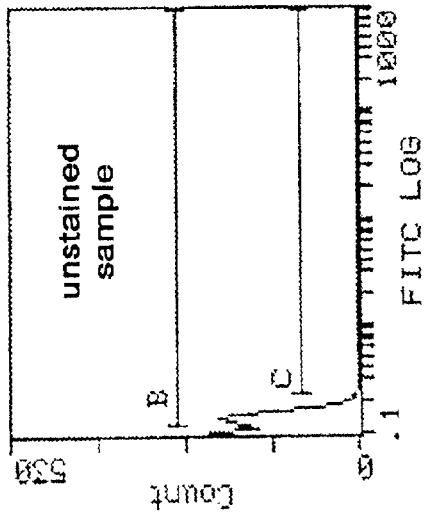
Figure 3D:
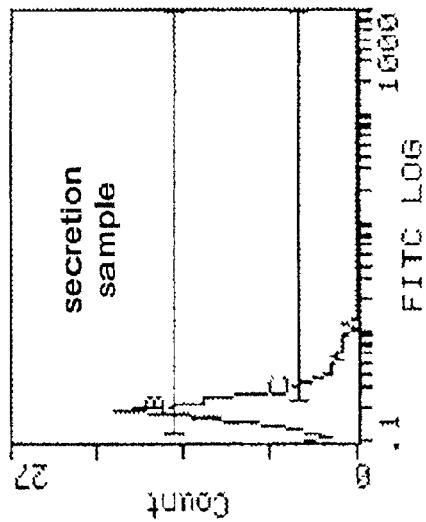
Figure 3E:
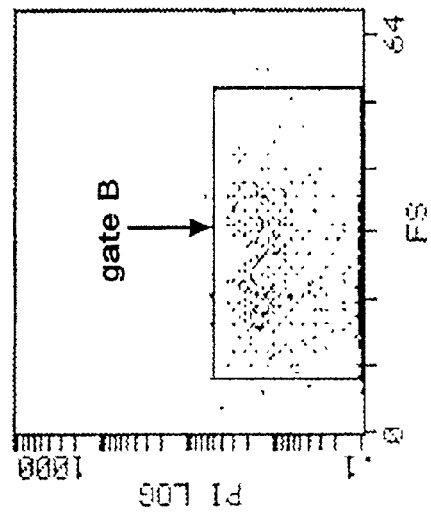
Figure 3F:
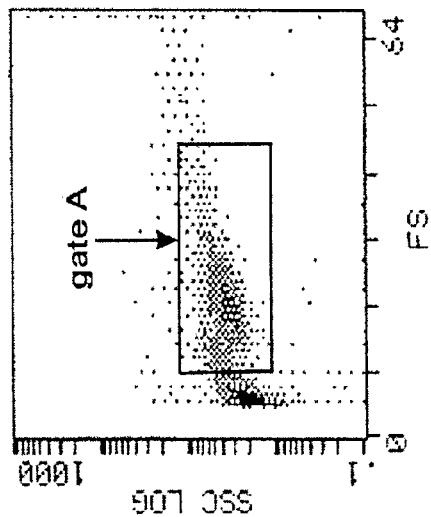

By plotting cytokine concentration vs. the corresponding average mean fluorescence of microdrops (after subtracting the background fluorescence value in the negative control), we generated titration curves for the average amount of cytokine detectable per microdrop. From the titration curve, we determined the lowest concentration of cytokine that resulted in fluorescence signal (above the negative control). One representative titration curve for detecting mrIFNγ labelled with PE-conjugatedantibody is shown in FIG. 2. Average mean fluorescence used to generate titration curves for rmIFNγ are summarized in Table 2. The level of mean fluorescence measured in unoccupied microdrops made from CelBioGel-1 and CelBioGel-2 correlated with cytokine concentration and the response was linear over the range of concentrations tested (1 ng/ml to 100 ng/ml). CelBioGel-2 demonstrated higher sensitivity. Using both agarose matrices, the end-point of the assay, which was the lowest concentration of cytokine detectable over background (negative control), varied from >100 to 10 ng/ml or: >125fg/microdrop when CelBioGel-i was used and 12.5fg/microdrop when CelBioGel-2 was used.

TABLE 2

Cytokine detection levels in solution using unoccupied microdrops labelled with capture and reporterantibodydetermined by flow cytometry

| Cytokine | Fluorochrome label of detection Ab | Encapsulation matrix | Mean fluorescence corresponding to cytokine concentration | | | | | | Detection level | |
|---|---|---|---|---|---|---|---|---|---|---|
| | | | 100 (ng/ml) | 50 (ng/ml) | 10 (ng/ml) | 5 (ng/ml) | 1 (ng/ml) | 0 (ng/ml) | ng/ml | fg/microdrop |
| mrIFNγ | FITC | CelBioGel ™-1 | 0.473 | 0.267 | 0.229 | 0.17 | 0.12 | 0.1 | >100 | >125 |
| mrIFNγ | FITC | CelBioGel- ™-2 | 43.86 | 20.36 | 2.53 | 1.7 | 1.21 | 1.62 | 10 | 12.5 |

We estimate that, on average, one 40 μm microdrop generated using CelBioGel-2 (~3×10$^{-8}$ ml volume) contains 6×10$^8$ molecules of biotin. After loading microdrops with streptavidin (3×10$^7$ molecules/microdrop), all the biotinylated captureantibodyin a 20 μg aliquot (~10$^7$ molecules/microdrop) are bound to the agarose matrix. In our experiments, even during a long incubation (18 hr), individual single cells secreted only small amounts of cytokines (on average from 1.8 to 35 fg/cell/microdrop). The molecular weight of the cytokines we tested are: mrIFNγ~17 kDa, mrIL-4~14 kDa, and mrIL-6~21.7 kDa. Calculations using Avogadro's number show that 1 fg of IL-6 contains ~3×10$^4$ molecules. Assuming a 1:1 ratio of analyte to detector, saturation of all binding sites in an individual microdrop (molecules of biotinylated antibody immobilized in the agarose matrix) would on average require at least 333.3 femtograms of secreted cytokine, which is in excess of the secretion levels detected in our experiments with primary cells (on average 1.8–35 fg/cell/microdrop after incubating for 18 hr). The reported level of cytokine secreted by individual cells (0.2–8 fg/cell of GM-CSF per 1 hr or 144 fg per 18 hr) (7) are ordinarily low and, therefore, we do not expect saturation of capture sites using our assay conditions. Assuming similar conditions for performing the secretion assay, the fluorescence intensity of occupied microdrops should reflect the amount of cytokine secreted by single cells during the secretion incubation time and the relative level of cytokine secretion can be estimated using the titration curve, approximating quantitation.

The effect of CelBioGel, CelBioGel-2 and CelBioGel-3 on the detection limit of the microdrop secretion assay was also evaluated using transfected CHO cells secreting high levels of mIgG1 (>20 μg/ml). Flow cytometry results are presented in Table 3. Although similar percentages of secretors were detected for CelBioGel-2 and CelBioGel-3 (approximately 99.5%), mean FITC fluorescence intensity (MFI) was significantly higher for CelBioGel-3 (144.91 vs 38.67), indicating a higher assay detection limit using CelBioGel-3. Of the three types of CelBioGel, CelBioGel-1 was the least sensitive. Only 81.24% of secretors were detected. In addition, MFI was low (10.63).

TABLE 3

Flow cytometry results of the microdrop Secretion Assay performed using transfected CHO cells secreting mIgG1 and different types of CelBioGel ™ (CelBioGel-1 ™, CelBioGel-2 ™ and CelBioGel-3 ™).

| | CelBioGel1 | | CelBioGel-2 | | CelBioGel-3 | |
|---|---|---|---|---|---|---|
| Samples | % positive | MFI | % positive | MFI | % positive | MFI |
| Negative Control | — | 1.29 | — | 1.61 | — | 2.83 |

TABLE 3-continued

Flow cytometry results of the microdrop Secretion Assay performed using transfected CHO cells secreting mIgG1 and different types of CelBioGel ™ (CelBioGel-1 ™, CelBioGel-2 ™ and CelBioGel-3 ™).

| | CelBioGel1 | | CelBioGel-2 | | CelBioGel-3 | |
|---|---|---|---|---|---|---|
| Samples | % positive | MFI | % positive | MFI | % positive | MFI |
| Positive control | — | 79.35 | — | 291.1 | — | 450.8 |
| Secretion 15 min | 81.25% | 10.63 | 99.5% | 38.67 | 99.6% | 144.91 |

Similar experiments were performed using transfected NSO cells with low secretory activity (<1 μg/ml). Flow cytometry results are presented in Table 4. The detection limit was higher using CelBioGel-3. Compared to CelBioGel-2, the percentage of secretors detected and Mean Fluorescence Intensity was approximately 3 times higher using CelBioGel-3.

TABLE 4

Flow cytometric results of the microdrop Secretion Assay performed using transfected NSO cells and different types of CelBioGel (CelBioGel-2 and CelBioGel-3).

| | CelBioGel-2 | | CelBioGel-3 | |
|---|---|---|---|---|
| SAMPLES | % positive | MFI | % positive | MFI |
| Negative control | — | 0.918 | — | 1.04 |
| Positive control | — | 24.7 | — | 63.3 |
| Secretion 1 hr | 7.8% | 1.3 | 23% | 3.26 |

3. Detection of hrIL-4 Secreting Transfected CHO Cells

To optimize the secretion assay, we initially used a transfected CHO cell line known to reproducibly secrete about 200 ng per ml of hrIL-4. After culturing cells for 3 days until they reached 75% confluency, we performed the microdrop cytokine secretion assay using 1×10$^6$ cells and CelBioGel-1. After a 2 hr incubation, microscopy revealed that the majority of occupied microdrops were saturated and bright FITC fluorescence was visible in unoccupied microdrops indicating assay "crosstalk" (diffusion of secreted cytokine in excess of the saturated binding sites). We, therefore, used a 1 hr incubation for the assay and histograms of one representative experiment (of five) are shown in FIG. 3. Compared to the unstained sample (panel 1), incubation with FITC-labelled detection antibody resulted in low background fluorescence (0.34) in the negative ("no capture") control (panel 2) from non-specific binding. Microdrops in the positive control (25 ng/ml of hrIL-4, marker C, panel 3) exhibited significantly higher fluorescence (11.6). After incubating the sample for 1 hr, the subpopulation of microdrops occupied by single cells was gated using FS vs SSC dot plot (gate A, dot plot 4) and included for further data acquisition. Next, we discriminated viable (PI negative) cells (gate B, dot plot 5) using FITC fluorescence. Both the percentage and the mean fluorescence of positive events were determined by subtracting the corresponding values from the negative control. 26% of the encapsulated cell population secreted varying amounts of hrIL-4 as shown under marker C, panel 5. Cell viability assessed by Trypan Blue staining before experimentation and by PI staining during flow cytometry was high (98%) and was unaffected either by encapsulation or by secretion assay procedures. Results showed that if the cytokine level is high, as expected using transfected cells, positive microdrops can easily be detected after a short (1 hr) secretion incubation.

4. Detection of Cytokine Secretors in an Activated Murine Antigen-specific T Cell Line Next, we detected three different cytokines produced by an antigen-specific cell line. After growing cells in bulk culture for 48 hr, we tested supernatant using the microdrop assay format (microdrop supernatant control) and determined the relative amounts of cytokines secreted by the cells as: ~30 ng/ml of IFNγ, ~5 ng/ml of IL-4, and ~15 ng/ml of IL-6. Cell viability, assessed by Trypan Blue staining, ranged from 72% to 80%. Reduced cell viability was probably the result of activation-induced apoptosis and the presence of dead (or dying) mitomycin C treated feeder cells in the sample. Using the microdrop secretion assay and flow cytometry, we determined the percentage of cells secreting each individual cytokine and the mean fluorescence intensity corresponding to the average amount of cytokine secreted per cell after incubating for both 3.5 and 18 hr.

Figure 4:
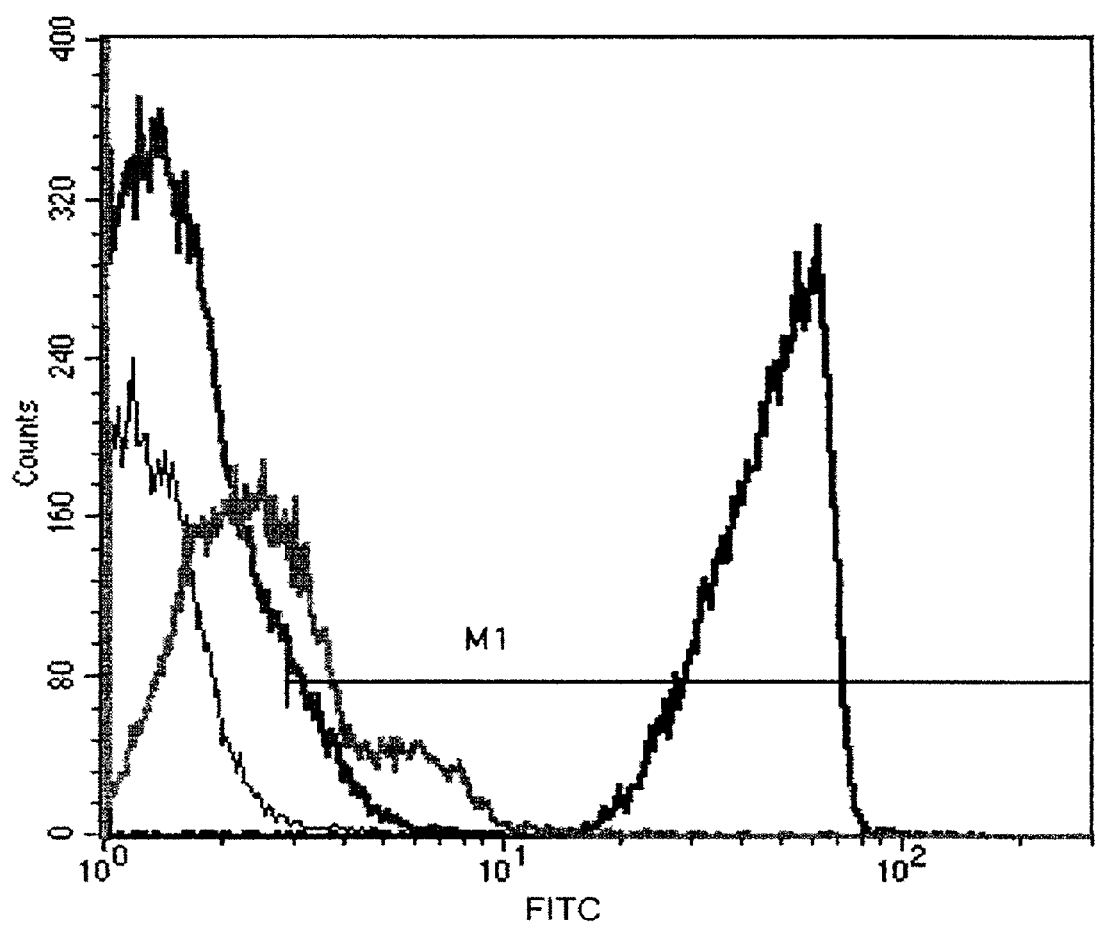
FIG. 4. Flow cytometric analysis of IL-4 secretion by activated antigen-specific T cells. The black lit histogram shows "no capture" (negative control Marker M1 was set to identify events with positive (higher than in the negative control) FITC fluorescence. The blue line histogram represents positive control (mrIL-4 at 10 ng/ml). 3.2% of positive events we detected after a 3.5 hr incubation (the red lit histogram) while 20.87% (the green line histogram were detected after an 18 hr incubation. Proportion increase of mean FITC fluorescence indicates increase cytokine secretion by detected cells.

Sub-populations of cells secreting each cytokine (1.26% IFNγ, 3.32% IL-4, and 1.38% IL-6) were detected after a short (3.5 hr) incubation. By extrapolating values of mean fluorescence from the cytokine titration curves, we estimated the average relative level of cytokine secreted by individual cells as: ~12.5 fg for IFNγ, ~1.8 fg for IL-4, and ~2.0 fg for IL-6, respectively. After increasing the incubation time to 18 hr, the frequency of cytokine secreting cells increased as follows: IFNγ (from 1.26% to 18.5%), IL-4 (from 3.32% to 20.87%) and IL-6 (from 1.38% to 15.55%). The mean fluorescence and, thus, the average relative amount of secreted cytokine also increased significantly (IFNγ: from ~12.5 fg to 35 fg, and IL-4: from ~1.8 fg to 3.6 fg, respectively). Although, after lengthening the incubation time, the frequency of IL-6 secreting cells increased from 1.38% to 15.55%, the increases in the relative levels of cytokine secretion were not significant (~2.0 fg/microdrop vs ~2.4 fg/microdrop). 90% of the FITC-positive occupied microdrops were PI-negative, indicating high cell viability throughout the assay procedures. Histograms from one representative experiment to detect IL-4 after incubating for both 3.5 and 18 hr are shown in FIG. 4 and the estimated frequency of IFNγ, IL-4, and IL-6 sub-populations are presented in Table 5.

TABLE 5

Flow cytometric analysis of cytokine secretion by activated antigen-specific T cells using the microdrop secretion assay format.

| Cytokine detected | Frequencies of cytokine secreting cells (% positive events) | |
|---|---|---|
| | 3.5 hr secretion incubation | 18 hr secretion incubation |
| mrIFNγ | 1.26% | 18.5% |
| mrIL-4 | 3.32% | 20.87% |
| mrIL-6 | 1.38% | 15.55% |

5. Detection of IFNγ and IL-6 Secreting Cells Among Activated Mouse Naïve Splenocytes Due to the anticipated low frequency of activated cells in primary culture and their inherent low level of cytokine secretion, we stimulated naive mouse splenocytes in vitro with either ConA or PHA for 24 hr prior to performing the microdrop secretion assay. Results using both mitogens were essentially the same. Analysis of microdrop supernatant controls showed that after 24 hr in culture, on average, splenocytes secreted ~20 ng/ml of IFNγ and ~10 ng/ml of IL-6. Cell viability, determined by the Trypan Blue exclusion assay before and after encapsulation, was high (>98%). After incubating with capture antibody and incubating encapsulated cells for 3.5 and 18 hr, samples were stained with either FITC-labelled anti-mouse IFNγ or PE-labelled anti-mouse IL-6 Abs (both at final concentrations of 5 μg/ml).

Although sub-populations of cytokine secreting cells were not detectable by flow cytometry after incubating for 3.5 hr, both IFNγ and IL-6 secreting cells were discriminated after increasing the incubation to 18 hr. As expected, compared to the antigen-specific cell line and transfected cells, the frequency of positive cells and the average mean fluorescence of positive microdrops were lower for both cytokines. In this heterogeneous population of stimulated naive splenocytes, we detected a 4.72% sub-population of cells secreting IFNγ and a 4.43% sub-population secreting IL-6. By extrapolating corresponding mean fluorescence values from the titration curve, the estimated average amounts of cytokines secreted by individual cells were ~11.5 fg/microdrop for IFNγ and ~2 fg/microdrop for IL-6, respectively. Flow cytometric analysis of PI staining showed that cell viability was high throughout the experiment (>98%).

Figure 5A:
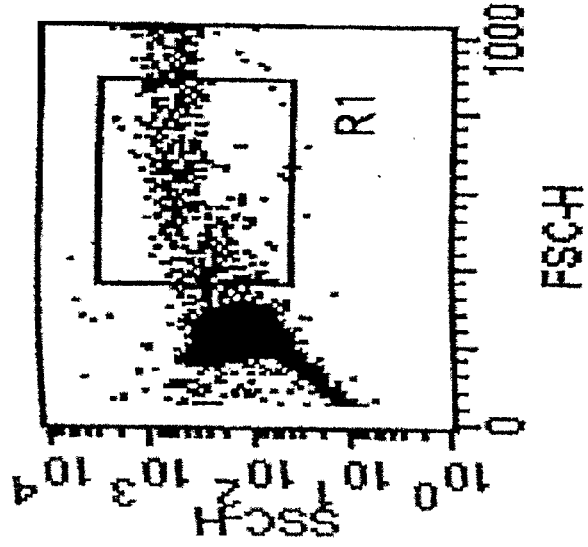
FIG. 5. Simultaneous detection of viable CD3 positive IFNγ secreting cells. After stimulating in vitro with antigen in the presence of mitomycin C treated autologous feeder cells and mrIL-2, we performed the GMD IFNγ secretion assay with $1 \times 10^6$ encapsulated cells. Cells were incubated with FcBlock™ and PE-labeled mouse anti-CD3 Ab (10 µg/ml) prior to flow cytometric analysis. Unoccupied GMDs were discriminated from occupied GMDs using FSC and SSC (panel A). Only GMDs occupied by viable (PI negative) cells were included in data acquisition (RI gate, panel A). Dot plots of the negative control and the IFNγ secretion sample (both stained with anti-IFNγ/FITC (FL-1) anti-CD3/PE (FL-2) Abs) are shown in panel B and panel C, respectively.
Figure 5B:
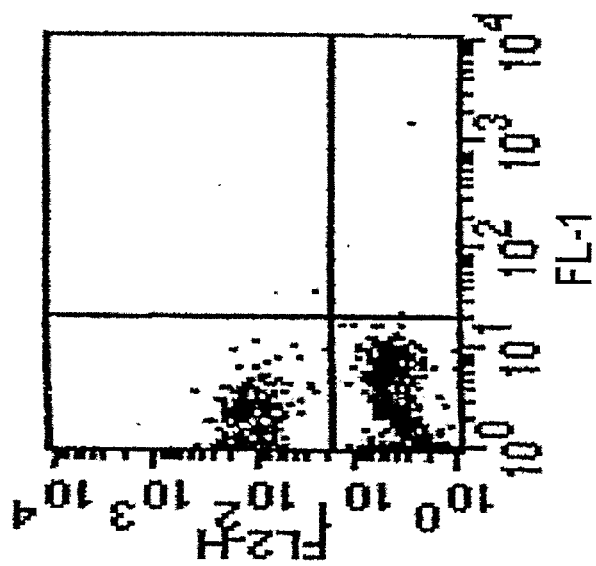
Figure 5C:
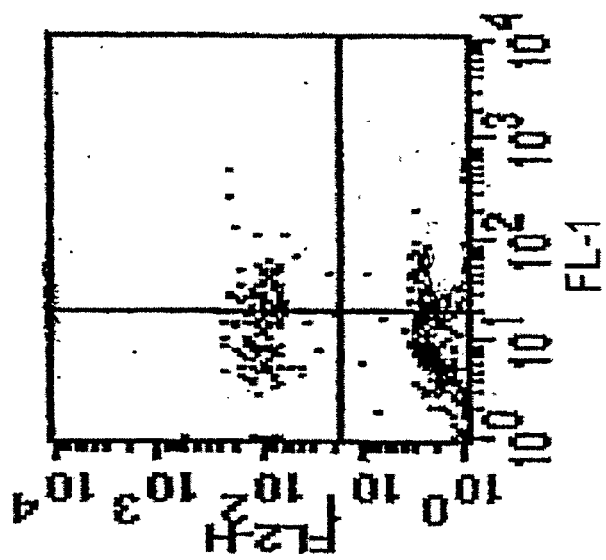
Figure 7A:
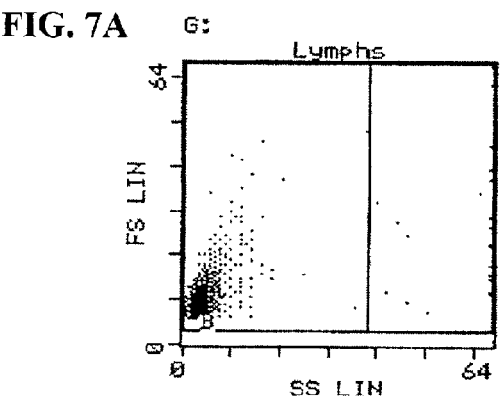
FIG. 7. Simultaneous detection of CD3, CD4 and CD69 cell surface expression and IFNγ secretion by encapsulated freshly isolated human PBMCs using four color flow cytometry. Human PBMCs unstimulated or stimulated in vitro for 24 hr with PHA (5 µg/ml) were encapsulated in CelBioGel-R$^{-1}$. Lymphocyte subsets were identified by immunophenotype and IFNγ secretion using four color flow cytometry. Representative histograms from unstimulated cells used as negative controls for all tested parameters are shown in 1–4 A. CD3$^+$CD4$^+$ cells were identified among both unstimulated and stimulated lymphocytes (3-A and 3-B). In addition, a 79.6% sub-population of stimulated lymphocytes expressing CD69 (2-B, under marker E) and a 9.6% sub-population secreting IFNγ (4-B, under marker I) were identified after subtracting background from unstimulated controls (1.3%, 2-A, under marker E and 1.3%, 4-A, under marker I).
Figure 7B:
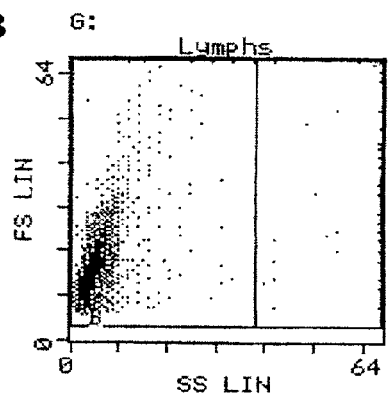
Figure 7C:
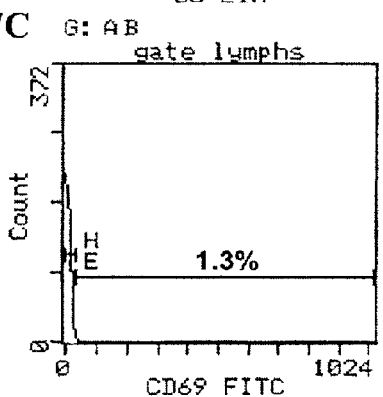
Figure 7D:
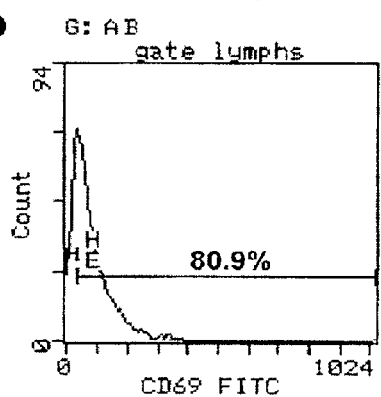
Figure 7E:
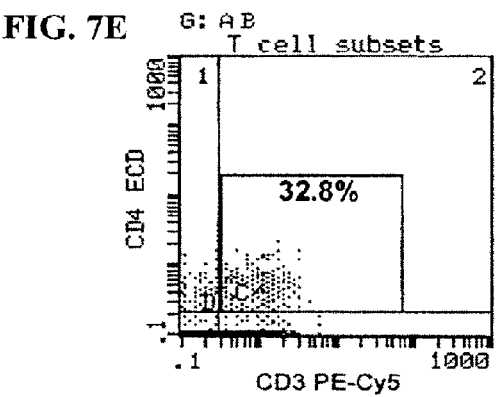
Figure 7F:
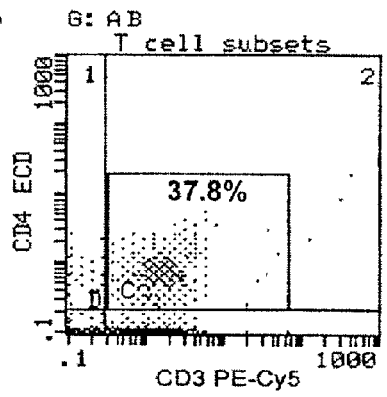
Figure 7G:
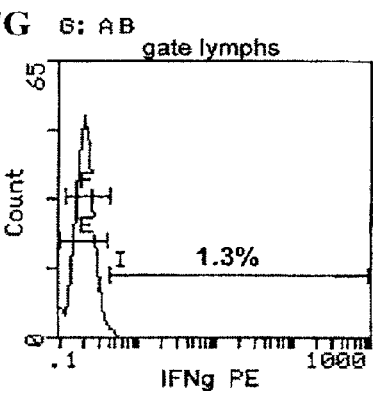
Figure 7H:
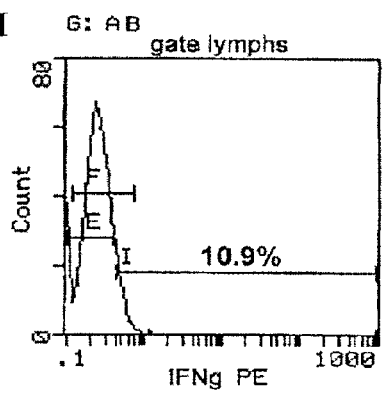

6. Simultaneous Detection of Secreted Cytokine and Cell Surface Marker We next performed experiments to simultaneously detect secreted IFNγ and CD3 surface expression in mouse antigen-specific T cells. Cells were re-stimulated with M1081 peptide in the presence of mitomycin C treated autologous feeder cells and mrIL-2 and maintained in culture for 2 days, as described in Materials and Methods. Cell viability before experimentation was ~74%. To perform the microdrop secretion assay, we incubated cells for 18 hr after encapsulation. Using two-color flow cytometry, we discriminated a sub-population of CD3$^+$ cells secreting IFNγ (FIG. 5) by gating on microdrops occupied by single viable (PI negative) cells (R1 gate, panel A) and measuring FITC (FL-1) and PE (FL-2) fluorescence.

Two sub-populations were detected in the "no capture" (negative) control (panel B): CD3$^+$ cells (45.9% in the upper left quadrant) and CD3$^-$ cells (53.88% in the lower left quadrant); both had low levels of background FITC fluorescence (1.49 and 2.56, respectively). However, in the secretion sample (panel C), a 14.8% sub-population of CD3$^+$ activated antigen-specific cells was detected (double-positive events in the upper right quadrant). 29.4% of CD3$^+$ cells did not secrete IFNγ (single-positive events in the upper left quadrant). IFNγ secreting cells were also detected among the CD3$^-$ sub-population (5.4% in the lower right quadrant). Most of these events were probably B lymphocytes, NK cells, or macrophage and dendritic cells derived from mitomycin C treated autologous feeder cells. Double-negative events (49.7% CD3$^-$ cells), which did not secrete IFNγ, were located in the lower left quadrant.

7. Recovery and Propagation of Cytokine Secreting Cells

We recovered both transfected CHO cells secreting hrIL-4 and activated mouse antigen-specific cells secreting IFNγ by FACS. After sorting a sub-population (5%) of highly fluorescent microdrops occupied by single viable CHO cells secreting hrIL-4, cells were released from microdrops by agarase treatment (1 U/ml), and incubated for 48 hr in a 24-well plate. Cells released from microdrops adhered to the bottom of the well and grew as a monolayer. Cells were then transferred to a 25 cm culture flask, incubated until confluency, and re-screened after 2 weeks using the microdrop secretion assay. Next, we sorted a sub-population (18.5%) of activated mouse antigen-specific cells secreting IFNγ. 50,438 positive events (microdrops occupied by single viable cytokine secreting cells) were collected. After sorting, encapsulated cells were pooled and incubated in medium containing mrIL-2 (10 ng/ml) and agarase (3 U/ml) for 18 hr, when the majority of the cells were released from microdrops. After adding complete medium (5 ml) mixed with conditioned medium (in a 3:1 ratio) and supplemented with the antigen (M1081 peptide) at 10 μg/ml, mitomycin C treated autologous feeder cells (1:1) and mrIL-2 (10 μg/ml), the flask was returned to the incubator for an additional 6 days prior to re-stimulation. Viability and proliferation, assessed every other day via Trypan Blue staining and counting in a hemocytometer chamber, indicated the presence of an increasing population of viable antigen-specific cells.

8. Simultaneous Detection of mrIFNγ and mrIL-4 in Unoccupied Microdrops Using Two-Color Flow Cytometry.

After labeling with a mixture of biotinylated anti-IFNγ and anti-IL-4 Abs (both at final concentration of 5 μg/ml), microdrops were incubated with a mixture of purified cytokines: mrIFNγ (100 ng/ml) and mrIL-4 (25 ng/ml). In the negative ("no capture") control ((FIG. 6, panel A), background fluorescence was very low for both FL-1 (FITC) and FL-2 (PE) fluorescence; the majority of microdrops (99%) were double negative and located in the lower left quadrant. When mrIFNγ (panel B) or mrIL-4 (panel C) were detected individually (incubated with only anti-IFNγ/PE or with only anti-IL-4/FITC, both at 5 μg/ml), positive microdrops exhibiting high FL-2 (541.48) or FL-1 (155.06) fluorescence were located in the upper left or lower right quadrants, respectively. When detecting both cytokines simultaneously (incubating with a mixture of fluorochrome-labelled Abs, both at 5 μg/ml), 84% of microdrops were double positive (panel D, the upper right quadrant of the dot plot) with mean fluorescence of 189.5 (FL-1) and 636 (FL-2). The levels of secreted cytokine detected simultaneously were similar to the levels measured individually, suggesting that the microdrop immunoassay can be used to detect more than one cytokine secreted by individual encapsulated cells without compromising assay sensitivity.

9. Detection of Multiple Cell Surface Markers and a Secreted Cytokine Simultaneously Using Four Color Flow Cytometry Using encapsulated human PBMCs (unstimulated and stimulated with PHA), we successfully detected CD3, CD4, and CD69 cell surface expression and IFNγ secretion after a 4 hr incubation. Four color analysis was performed using an EPICS Elite (Coulter Corp.). Fluorochrome-labelled samples were excited by the 488 nm spectral line of an argon laser. To identify lymphocyte sub-populations by immunophenotype and IFNγ secretion, we first identified lymphocytes using forward vs. side scatter. CD3 and CD4 fluorescence were then detected on cells within the gated lymphocyte population. CD69 expression was used to identify activated cells (FITC) and anti-IFNγ antibody was used to identify cytokine secreting cells (PE). Histograms from this experiment demonstrate that using the microdrop assay format and four color flow cytometry, surface markers and secreted cytokine can be detected simultaneously within defined lymphocyte sub-population after in vitro stimulation of human PBMCs with PHA (FIG. 7).

The sub-population of microdrops occupied by lymphocytes was identified using a dual parameter dot plot (SSC vs. FS, histograms 1-A and 1-B in FIG. 7). An increase in forward scatter can be seen with mitogen-stimulated lymphocytes as expected. Although sub-populations of CD3$^+$ CD4$^+$ cells were identifiable in both unstimulated (32.8%, FIG. 7, histogram 3-A, quadrant C2) and stimulated PBMCS samples (37.8%, FIG. 7, histogram 3-B, quadrant C2), as expected, CD69 expression was only detectable in the population of stimulated lymphocytes. After subtracting the background level of the unstimulated control (FIG. 7, histogram 2-A, 1.3% marker E), we identified a 79.6% sub-population of lymphocytes expressing CD69 with mean FITC fluorescence of 102.3 (FIG. 7, histogram 2-B, marker E).

In addition, we identified a 9.6% sub-population of stimulated lymphocytes secreting IFNγ (10.9%–1.3% =9.6%- FIG. 7, histograms 4-A and 4-B, marker I).

Figure 8:
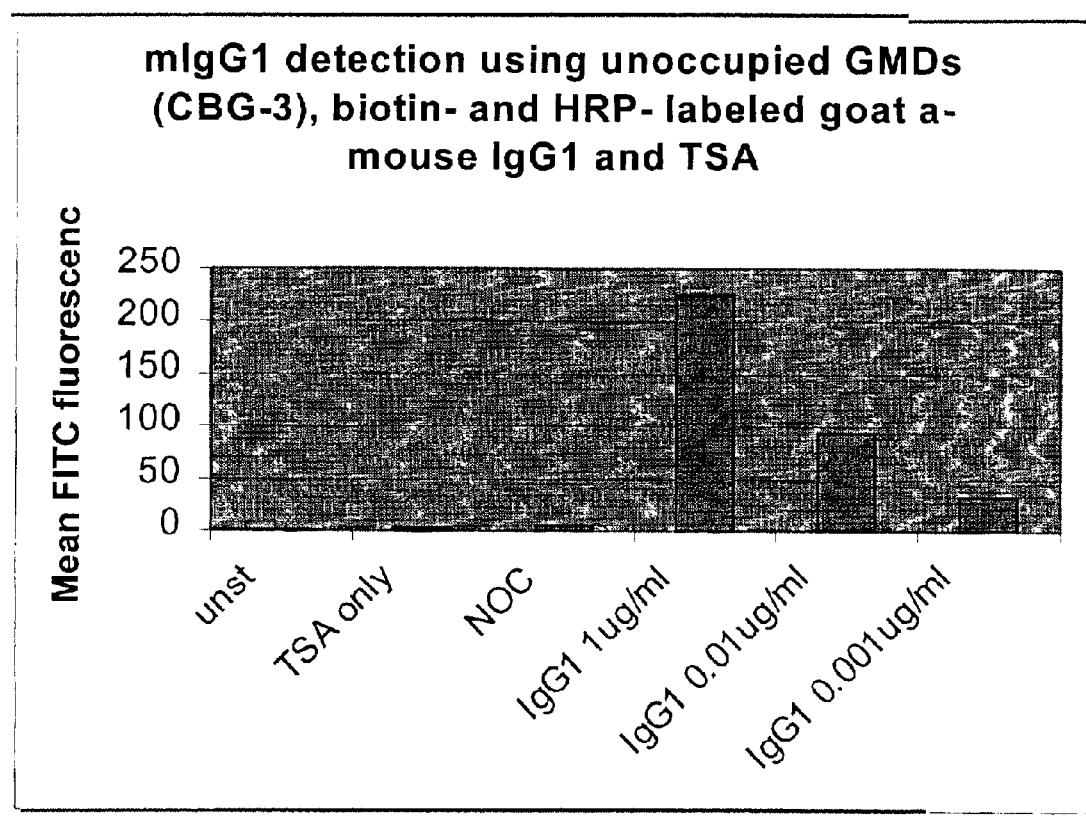
FIG. 8. mIgG1 detection using unoccupied GMDs (CBG-3), biotin- and HRP-labelled goat anti-mouse IgG1 and TSA

Neither the encapsulation procedure nor the microdrop Secretion Assay affected cell viability as determined by a Trypan Blue exclusion assay 10. Detecting Secreted Products Released by Individual Cells Using Enzyme-Linked Immunoassay Format, TSA Signal Amplification Reagent, and Flow Cytometry HRP-labelled detection antibody and TSA amplify the signal at least 10 fold allowing detection of pg/ml levels. This sensitivity is particularly useful for detecting cytokine-secreting cells because the majority of these regulatory factors are secreted transiently in small quantities. To demonstrate the feasibility of the proposed approach we detected different amounts of purified mouse IgG1 in the supernatant using unoccupied microdrops (CelBioGel-3). Microdrops were incubated with streptavidin (50 μg/ml) for 15 min at RT and washed 3 times with HBSS. Then, incubatingwith biotinylated goat a-mouse IgG1 (H+L) at a concentration of 10 μg/ml was performed for 15 min at RT. After washing with HBSS 3 times, microdrops were incubated with different concentrations of purified mouse IgG1 (1.0 μg/ml, 0.01 μg/ml, and 0.001 μg/ml) for 20 min at RT and then washed again in HBSS 3 times. Detection antibody (HRP-labelled goat a-mouse IgG1, Fc fragment specific) was added to all samples at final dilution of 1:200. After incubating for 20 min at RT and washing 3 times with HBSS, FITC-labelled TSA reagent was added at a final dilution of 1:200. After a 10 min incubation at RT, microdrops were washed 3 times in HBSS and all samples were analyzed by flow cytometry along with three controls: 1) unstained microdrops, 2) TSA reagent only, and 3) negative (no capture Ab) control. Results of this experiment demonstrate feasibility of using the proposed microdrop assay for extracellular detection of secreted products are shown in FIG. 8.

Low background fluorescence was seen in all three controls (1.27, 2.87, and 4.6, respectively). While mIgG1 at 1 μg/ml and 0.01 mg/ml generated MFI of 224.78 and 93.14, respectively, mIgG1 at concentration of 0.001 μg/ml (1 ng/ml) was still clearly detectable (MFI 31.98).

11. Detection of In-vitro Induced IgG Isotype Switching Rate Among CRL-8018 Hybridoma Cells Using Sequennal Sublining Experiments were performed with CRL-8018 hybridoma cell line as described in Materials and Methods. We determined that for the CRL-8018 cell line, the most effective in-vitro conditions were: a) retinoic acid (at 100 nM), which induced a witch to mIgG1 and mIgG2b, or b) purified antigen (HBsAg at 1 μg/ml) combined with mrIL-4 (at 10 ng/ml), which induced a switch to mIgG1. Sequental sublining was performed as described in Materials and Methods. $1 \times 10^6$ cells were resuspended in 200 ml of growth medium supplemented with 100 nM of retinoic acid ($5 \times 10^3$/ ml) and plated out in ten 96-well plates at a density of 1,000 cells/well (0.2 ml/well). After 5 days of incubation at 37° C. and 5% $CO_2$, mIgG isotype specific ELISA was performed with cell culture supernates. Cells from two positive wells were plated out in 96-well plates at a density of 100 cells/well (25 plates). Five rounds of the above procedure were performed: 1,000 cells/well, 100 cells/well, 10 cells/ well, and 1 cell/well. Results of one representative experiment are shown in Table 6. After plating out cells at a density of 1,000 cells/well in ten 96-well plates, supernatant ELISA revealed that 6 wells (0.6%) were low positive for mIgG. This indicates that the rate of isotype switching was ~0.0006%. About two months, 110 plates and 10,560 supernates for mIgG isotype specific ELISA were required for the assay.

TABLE 6

Detection of mIgG switch variants in CRL-8018 hybridoma cell line by sequential sublining after in-vitro induction with retinoic acid (100 nM)

| Plating density | 1,000 cells/well | 100 cells/well | 10 cells/well | 1 cell/well |
|---|---|---|---|---|
| mIgG positive wells | 6 | 298 | 564 | 2188 |
| % positives[a] | 0.6% | 12.4% | 23.5% | 91.2% |

[a]Percent of 960 wells plated at 1,000 cells/well and 2400 wells at lower densities.

Results of Microdrop Isotype Capture and Isolation Assay for Detecting Small Sub-populations in Artificial Cell Mixtures The sequential (two-step) microdrop isotype capture and isolation assay was used in experiments with IgM secreting CRL-8018 hybridoma cell line spiked with IgG3 secreting TIB-114 hybridoma cells. After plating CRL-8018 cells at $1 \times 10^4$/ml in six 75 cm² flasks (25 ml of DMEM+ 10% FBS/flask) for 7 days, cells were harvested and mixed with TIB-114 cells at 0.1% (experiment 1), 0.01% (experiment 2), and 0.001% (experiment 3). CelBioGel-3 was used to encapsulate cell mixtures: $2 \times 10^6$ cells in experiment 1 (single cell encapsulation), $25 \times 10^6$ cells in experiment 2, and $50 \times 10^6$ cells in experiment 3 (both multiple cell encapsulations). One round of the microdrop isotype capture and isolation was performed in experiment 1 and the two-step assay format was used in experiments 2 and 3, as described in Materials and Methods. Isolated cells were propagated in culture and supernates were analyzed using IsoStrip™ dipsticks, as described above. In experiments 2 and 3, both mIgM and mIgG3 were detected in supernates of cells recovered after the first round of sorting. However, mIgG3 and only traces of mIgM were detected after a sequential second round of sorting. Single cell encapsulation of $1 \times 10^6$ IgM secreting cells spiked with 0.1% of IgG3 secreting hybridoma in experiment 1 resulted in isolation of only mIgG3 secreting cells by FACS. Results of experiments are summarized in Table 7.

TABLE 7

Results of the microdrop isotype capture and isolation assay for detecting smallsub-populations of mIgG3 secreting hybridoma cells mixed with mIgM secreting hybridoma cell line.

| Proportion of mIgG3 secreting cells among mIgM secreting hybridoma | Total number of encapsulated cells | Mean number of cells per GMD | The first round of FACS % positive events detected | | Sequentional second round of FACS of single occupied GMDs % positive events detected | |
|---|---|---|---|---|---|---|
| Experiment 1 (0.1%) | $1 \times 10^6$ | 1.0 | 0.1% | 112.45 | — | — |
| Experiment 2 (0.01%) | $25 \times 10^6$ | 3.2 | 0.47% | 146.24 | 25.7% | 151.8 |
| Experiment 3 (0.001%) | $50 \times 10^6$ | 7.5 | 0.03% | 132.4 | 13.4% | 137.52 |

Determination of Spontaneous and in-vitro Induced Switching Rate Using the Microdrop Isotype Capture and Isolation Assay The Microdrop-based assay format was used to isolate in-vitro induced and spontaneous isotype switch variants from populations of IgM secreting CRL-8018 hybridoma cell line. Representative results of one experiment from five performed with each experimental condition are shown in Table 8. In the first round of experiments, we determined the rate of spontaneous isotype switching. $75 \times 10^6$ hybridoma cells were encapsulated using two aliquots of CelBioGel-3 and one 15-ml aliquot of CelMix™ as described in Materials and Methods. Approximately 60% of microdrops were occupied, with a mean of 9 cells per occupied The mIgG isotype capture assay was then performed and microdrops occupied by positive cells (0.02%) were isolated using FACS. Based on the number of cell encapsulated, the estimated rate of isotype switching was calculated to be 0.0013%. Microdrops were sorted into 1 well of a 12-well plate and incubated overnight in 1 ml of growth medium containing 5 U/ml agarase. After overnight incubation, the majority of actively dividing cells had outgrown microdrops. 1 ml of fresh medium was added to the well and cells were incubated for an additional 5 days. The second round of the microdrop isotype detection and isolation assay was performed by encapsulating 1×10$^6$ cells using single cell encapsulation conditions. 24.6% of occupied microdrops contained mIgG secreting cells. The sub-population of microdrops with the highest fluorescence (3.5%) were isolated by FACS.sub-population After overnight incubation in the presence of 5 U/ml of agarase, sorted cells were resuspended in complete medium and cloned by plating out in ten 96-well plates at a density of 1 cell/well. In two weeks, of 960 wells tested, 785 (81.7%) were scored positive by supernatant mIgG isotype ELISA.

To demonstrate detection of in vitro induced isotype switching, CRL-8018 hybridoma cells were grown for 5 days in complete medium containing 100 nM of retinoic acid. The presence of isotype switched cells was determined using IsoStrip™, which has a 0.1 µg/ml detection limit. For wells containing less than 0.1 µg/ml mIgG, multiple cell encapsulation was performed. For wells containing greater than 0.1 µg/ml mIgG, conventional single cell encapsulation was performed. Multiple cell encapsulation using 25×10$^6$ cells resulted in ~55% microdrops occupancy, with a mean cell number of 2.5 cells/microdrop. 0.09% positive events were detected, and isolated cells subjected to a second round of encapsulation. 36.4% positive events were detected, and the sub-population exhibiting the highest mean fluorescence (2.9%) was isolated. For single cell encapsulation, 2×10$^6$ cells from mIgG-positive wells were used. CelMix both specific for human hepatitis B surface antigen (HBsAg) were detected, respectively. This demonstrates that isotype switched variants had the same antigen specificity as the original hybridoma cell line.

BIBLIOGRAPHY

1. Opal, Chest, 117(4):1162–1172. 2000.
2. Bakhiet, Clin Diag Lab Immunol, 6(3):415–419. 1999.
3. Lin,. Betaseron. In: Characterization of Biotechnology Pharmaceutical Products. Brown,et al. (eds), Dev Biol Stand. Basel, Karger, 96:97–104. 1998.
4. Baiter, Science, 286:205–206. 1995.
5. Clerici J Clin Invest, 91:759–765. 1993.
6. Klein AIDS, 11:1111–1118. 1997.
7. Collins Cytometry, 33:249–255. 1998.
8. Van den Berg, Transpl Int, 11(suppl 1):S318–S321. 1998.
9. Smith, Immunol Rev, 51:337–357. 1980.
10. Abbas, Nature, 383:787–793. 1996.
11. Maino, Clinical Immunol Newsletter, 16(6):95–98. 1996.
12. Paul, Cell, 76:241–251. 1994.
13. Mosmann J Immunol, 136:2348–2357. 1986.
14. Mosmann, Immunol Today, 17:138–146. 1996.
15. Powrie, Immunol Today, 14:270–274. 1993.
16. Sher, A. and Coffman, R. L. Regulation of immunity to parasites by T cells and T cell-derived cytokines. Ann Rev Immunol, 10:385–394. 1992.

TABLE 8

Flow cytometric results of the microdrop isotype capture and isolation assays for detecting and sorting small sub-populations of mIgG-switched mIgM secreting CRL-8018 hybridoma cells.

| | | | Detection of mIgG secreting cells using FACS | | | | |
|---|---|---|---|---|---|---|---|
| | | | The first round of FACS (all positive GMDs were sorted) | | Sequential second round of FACS of single occupied GMDs | | |
| | Total number of encapsulated cells | Mean number of cells per GMD | % positive events detected | FITC MFI | % positive events detected | FITC MFI | Sorted GMDs MFI (% pos) |
| Spontaneous isotype switch | 75 × 10$^6$ | 9.0 | 0.02% | 8.25 | 24.6% | 12.7 | 83.4 (3.5%) |
| In-vitro induced isotype switch (retinoic acid at 100 nM) | 25 × 10$^6$ mIgG >0.1 µg/ml | 2.5 | 0.09% | 17.93 | 36.4% | 11.3 | 75.2 (2.9%) |
| | 2 × 10$^6$ mIgG <0.1 µg/ml | 1 | 0.15% | 320.65 | — | — | — |

Determination of Antigen Specificity of Isotype-switched Cells Isolated Using the microdrop-based Assay To demonstrate antigen specificity of isotype switched cells isolated using the microdrop-based assay format, we used supernate ELISA-based mouse MonoAb ID kit (Zymed Laboratories). After coating 96-well plates with HBsAg (10 µg/ml), the procedure was performed according to the manufacturer's recommendations to determine isotype subclasses of antigen specific antibody: mIgG1 ($\gamma_1$ chain specific), mIgG2a ($\gamma_{2a}$ chain specific), mIgG2b ($\gamma_{2b}$ chain specific), mIgG3 ($\gamma_3$ chain specific), mIgA ($\alpha$ chain specific), mIgM ($\mu$ chain specific), mouse kappa light chain specific, and mouse lambda light chain specific. We tested supernates of CRL-8018 hybridoma cells grown in complete medium and switched cells isolated after in-vitro induction with retinoic acid (100 nM), mIgM ($\kappa$ chain specific) and mIgG1, and 17. Weaver, J. C. Gel microdroplets for microbial measurement and screening: basic principles. Biotech. and Bioengr. Symp. 17:185–195, 1986.
18. Weaver, J. C., Williams, G. B., Klibanov, A. and Demain, A. L. Gel microdrops: rapid detection and enumeration of individual microorganisms by their metabolic activity. Bio/Technology, 6:1084–1089. 1988.
19. Weaver, J. C., Bliss, J. G., Harrison, G. I., et al. In Methods: A Companion to Methods in Enzymology, Academic Press: San Diego, 2(3): 234–247. 1991.
20. Powell, K. T. and Weaver, J. C. Gel microdroplets and flow cytometry: rapid determination of antibody secretion by individual cells within a cell population. Bio/Technology, 8:333–337. 1990.
21. Weaver, Nature Medicine, 3(5):583–584. 1997.
22. Gray J. Immunol Methods, 182:155–163. 1995.

23. Akselband, 34th Annual Meeting of American Society of Microbiology, Worcester, Mass., Oct. 26–28, 1999.
24. Goguen, Nature, 363:189–90. 1993.
25. Nguyen, Cytometry, 21:111–119, 1995.
26. Ryan, J. Clin. Microbiol., 33:1720–26, 1995.
27. Weaver, In Flow cytometry applications in animal cell culture, Eds. Al-Rubeai and Emery, Marcel Dekker, New York, N.Y., 39–62, 1995.
28. Kenny, Bio/Technology, 13:787–790, 1995.
29. Gift, Nat. Biotech., 14:884–887, 1996.
30. Trnovsky Am. J. Hum. Genetics, 59, 4, A135, 1996.
31. FerranteSusceptibility testing and screening using a gel microdrop (GMD) based assay. Society for Industrial Microbiology, Northeast Branch, March 1997.
32. Weaver In ASM Manual of Industrial Microbiology and Biotechnology, 2$^{nd}$ edition, Eds. Demain A L and Davis J E, Am. Soc. Microbiol., Washington, D.C., pp. 114–118, 1999.
33. Gift, Cytometry 39:243–249, 2000.
34. HammillCytotechnology, 34:27–37. 2000.
35. Wadhwa In: Cytokines. A Practical Approach. pp.309–330. F. R. Balkwill (ed), IRL PRESS at Oxford University Press. Oxford, N.Y. 1991.
36. Crowther, Methods Mol Biol, 42:1–223. 1995.
37. Ogata, A J Immunol Methods, 148:15–21. 1992.
38. Shankar, ELISA. J Immunol, 18(4):371–388. 1997.
39. Carson, J Immunol Methods, 227:41–52. 1999.
40. Naylor, In: Cytokines. A Practical Approach. pp.31–50. F. R. Balkwill (ed), IRL PRESS at Oxford University Press. Oxford, N.Y. 1991.
41. Brenner, In: Cytokines. A Practical Approach. pp.51–59. F. R. Balkwill (ed), IRL PRESS at Oxford University Press. Oxford, N.Y. 1991.
42. Naylor, In: Balkwill R. F. (ed). Cytokines. A Practical Approach. Oxford Univ. Press, Oxford, p.35. 1995.
43. Carter, Curr Opin Immunol, 9:177–182. 1997.
44. Maino, Cytometry, 34:207–215. 1998.
45. SuniJ Immunol Methods, 212:89–98. 1998.
46. Openshaw J Exp Med, 182:1357–1367. 1995.
47. Jung, J Immunol Methods, 159:197–207. 1993.
48. Prussin, J Immunol Methods, 188:117–128. 1995.
49. Manz, Immunology, 92:1921–1925. 1995.
50. Holmes, J Immunol Methods, 230:141–147. 1999.
51. Brosterhus, Eur J Immunol, 29:4053–4059. 1999.
52. Scheffold, Eur Cytokine Netw, 9 (suppl 3): 5–11. 1998.
53. Akdis, Immunol Methods, 182:251–261. 1995.
54. Akdi, Eur J Immunol, 27:2351–2357. 1997.
55. Londei, In: Cytokines. A Practical Approach. pp.151–169. F. R. Balkwill (ed), IRL PRESS at Oxford University Press, Oxford, N.Y. 1991.
56. BrosterhusEur J Immunol, 29(12):4053–4059. 1999.
57. Waldrop, J Immunol, 161(10):5284–5295. 1998.
58. Zandstra Proc Natl Acad Sci USA, 94:4698–4703. 1997.
59. Petzer, J Exp Med, 183:2551–2558. 1996.
60. Perfetto Cytometry, 30:1–9. 1997.
61. WaldropJ Clin Invest, 99:1739–1741. 1997.
62. Maino Cytometry, 20:127–133. 1995.
63. Sedar, J Exp Med, 176:1091–1098. 1992.
64. Hsiech, Proc Natl Acad Sci USA, 89:6065–6069. 1992.
65. Hsiech Proc Natl Acad Sci USA, 90:10188–10192. 1993.
67. Dinarello. J Exp Med, 163:1433–1450. 1986.
68. Dinarello, C. A. Biology of interleukin 1. FASEB J 2:108–115. 1988.
69. Okusawa J Clin Invest, 81:1162–1172. 1998.
70. Hesse, Surg Gynecol Obstet, 166:147–153. 1988.
71. Moser, J Clin Invest, 83:444–455. 1989.
72. Allison, In Aggarwal. B., Puri, K.K. (eds). Human cytokines: their role in disease and therapy. Blackwell Science, pp. 689–713. 1995.
73. Eaves, Blood, 80:67a. 1992.
74. Ogawa, Blood, 81:2844–2853. 1993.
75. Mercken J Immunol Methods, 138:173–180. 1991.
76. Boot, J Immunol Methods, 106:195–202. 1988.
77. Muller, J Immunol, 131(2):877–881. 1983.
78. Kenney, J Immunol Methods. July 26; 121(2):157–66. 1989
79. Borrebaeck, Trends Biotechnol 1986, 4, 147.
80. Stavnezer, J. Science, 228:984–985. 2000.
81. Harlow, Antibodies: *A Laboratory Manual.* (eds. Harlow E., Lane D.) Cold Spring Harbor Laboratory, pp242 1988.
82. Spira, Clin Exp Immunol. 105(3):436–42. 1996
83. Spira, Methods of Hybridoma Formation (eds. Bartal A. H., Hirshaut Y) Humana Press, pp 385–391. 1987.
84. Pluschke, Eur J Immunol. 17(3):413–6. 1987
86. Weave, Nature Medicine. 3(5):583–585, 1997.
87. Powell Bio/Technology, 8:333–337, 1990.
88. Kenny,. Bio/Technology, 13:787–790, 1995.
89. Weaver, In Methods: a companion to methods in enzymology, Academic Press, San Diego, 2(3):234–247, 1991.
90. Weaver, In Flow cytometry applications in animal cell culture, Eds. Al-Rubeai and Emery, Marcel Dekker, New York, N.Y., 39–62, 1995.
91. Gray J. 1 mm. Meth., 182:155–163, 1995.
92. Hammill, Cytotechnology, 34:27–37. 2000.
93. Lin, M. and Chen, Y. B cell differentiation. II. Isotype potential of a single B cell. Cell Immunol, 150:343–352. 1993.

All publications and patent applications cited above are incorporated by reference in their entirety for all purposes to the same extent as if each individual publication or patent application were specifically and individually indicated to be so incorporated by reference. Although the present invention has been described in some detail by way of illustration and example for purposes of clarity and understanding, it will be apparent that certain changes and modifications may be practiced within the scope of the appended claims. Unless otherwise apparent from the context is apparent that the elements, steps, features and embodiments of the invention described in this application can be used in all combinations with each other.

What is claimed is:

1. A method of analyzing a secreted molecule, comprising:

encapsulating a cell in a microdrop wherein the microdrop comprises agarose molecules, first biotin molecules linked to the agarose molecules, capture molecules with affinity for a molecule secreted by the cell linked to second biotin molecules, and streptavidin linking the first and second biotin molecules, the first biotin molecules and the agarose molecules being in a molar ratio of less than 0.2 to 0.01 moles biotin per mole the agarose molecules, wherein the molecule is secreted from the cell and binds to the capture molecules thereby being retained within the microdrop; and detecting the secreted molecule.

2. The method of claim 1, wherein the molar ratio is 0.02 to 0.2.

3. The method of claim 1, wherein the concentration of the first biotin molecules in the microdrop is less than or equal to 42 micromolar.

4. The method of claim 1, wherein the encapsulating step encapsulates a plurality of cells in the microdrop.

5. The method of claim 1, wherein the encapsulating step encapsulates a single cell in the microdrop.

6. The method of claim 1, wherein the secreted molecule is a protein, hormone, or carbohydrate.

7. The method of claim 1, wherein the secreted molecule is a protein.

8. The method of claim 1, wherein the streptavidin and capture molecules are encapsulated into the microdrops at the same time as the cell.

9. The method of claim 1 wherein the streptavidin and captured molecules are incorporated into the microdrop after the encapsulating step.

10. The method of claim 1, wherein the microdrop further comprises second capture molecules with affinity for a second secreted molecule, the second capture molecules being linked to additional copies of the second biotin molecules.

11. The method of claim 10, wherein the cell secretes the second molecule.

12. The method of claim 1, wherein the detecting step is performed by contacting the microdrop with a detection reagent having specific affinity for the secreted molecule, and detecting binding of the detection reagent to the secreted molecule.

13. The method of claim 12, wherein the cell is a T-cell or a B-cell and the detection reagent is an antigen that specifically binds to the T-cell or B-cell.

14. The method of claim 12, wherein the detection reagent is labelled.

15. The method of claim 14, wherein a signal of the labelled detection reagent bound to the secreted molecule is proportional to the number of copies of the secreted molecule within the microdrop.

16. The method of claim 12, wherein the detection reagent is fluorescently labelled.

17. The method of claim 12, wherein the detection reagent is labelled with an enzyme that generates a product that is detected with a secondary detection reagent.

18. The method of claim 12, wherein the detecting step is performed by contacting the microdrop with a first detection reagent having specific affinity for the secreted molecule and a second detection reagent having specific affinity for the second secreted molecule wherein the first and second detection reagents are differentially labelled.

19. The method of claim 11, wherein the cell secretes a third secreted molecule, and the microdrop further comprises third capture molecules with affinity for the third secreted molecule, the third capture molecules being linked to additional copies of the second biotin molecules, and the method further comprises contacting the microdrop with first, second, third and fourth detection reagents having specific affinity for the secreted molecule, the second secreted molecule, the third secreted molecule and a cell surface marker respectively, and the detecting step detects the secreted protein, the second secreted protein, the third secreted protein and the cell surface marker.

20. The method of claim 12, wherein the detection step is performed by contacting the microdrop with a first detection reagent having affinity for the secreted molecule and a second detection reagent having affinity for a cell surface marker, and the first and second detection rpagents are differentially labelled.

21. The method of claim 20, wherein the detection reagent and the capture molecules specifically bind to different epitopes on the secreted molecule.

22. The method of claim 12, wherein more than one secreted protein and/or surface marker are detected simultaneously.

23. The method of claim 1, wherein the detecting step is performed by flow cytometry.

24. The method of claim 1, wherein the detecting step is performed by microscopy.

25. The method of claim 2, wherein the secreted protein is an antibody.

26. The method of claim 2, wherein the secreted protein is an antibody of IgG isotype and the capture molecules are antibodies specific for the IgG isotype.

27. The method of claim 2, wherein the secreted protein is a cytokine.

28. The method of claim 1, further comprising supplying an agent that induces the cell to secrete the secreted molecule.

29. The method of claim 28, wherein the inducing is performed after the encapsulating step.

30. The method of claim 28, wherein the inducing is performed before the encapsulating step.

31. The method of claim 7, wherein the cell comprises a vector comprising a nucleic acid segment encoding the secreted protein, the segment being operably linked to one or more regulatory DNA segments that effect expression of the secreted protein.

32. The method of claim 28, wherein the secreted protein is naturally secreted by the cell.

33. The method of claim 1, wherein the analyzing step is performed using flow cytometry.

34. The method of claim 1, wherein the analyzing step is performed using microscopy.

35. The method of claim 1, further comprising separating the cell from other cells using a cell sorter based on a fluorescent signal resulting from specific binding of fluorescently labelled detection reagents to secreted molecules and/or surface markers.

36. The method of claim 7, wherein the cell secretes first and second proteins, and the agarose comprises first and second capture molecules with affinity for the first and second proteins respectively, and the analyzing step comprises contacting the cell with first and second detection reagents that specifically bind to the first and second secreted proteins, and detecting the first and second proteins from signal of the first and second detecting reagents bound to the first and second secreted proteins.

37. A population of microdrops encapsulating cells, and the microdrops comprise matrix component molecules, first biotin molecules linked to the matrix component molecules, capture molecules with affinity for a protein secreted by the cell linked to second biotin molecules, and streptavidin linking the first and second biotin molecules, the first biotin molecules and the matrix molecules being in a molar ratio of 0.2 to 0.01 moles biotin per mole matrix component molecules.

38. The population of claim 37, wherein the molar ratio is 0.02 to 0.2.

39. The population of claim 37, wherein the concentration of biotin does not exceed 42 $\mu$M.

40. The population of claim 37, in which at least some microdrops encapsulate a single cell.

41. The population of claim 37, wherein the molar ratio of agarose and first biotin molecules is from 0.05 to 0.2 moles biotin per mole agarose.

42. In a method of analyzing a protein secreted by a cell in which the cell is encapsulated with a microdrop comprising biotinylated agarose the improvement wherein the molar ratio of biotin to agarose is 0.2 to 0.01 moles biotin per mole agarose.

* * * * *

UNITED STATES PATENT AND TRADEMARK OFFICE
CERTIFICATE OF CORRECTION

PATENT NO. : 6,806,058 B2
DATED : October 19, 2004
INVENTOR(S) : Jesperson et al.

It is certified that error appears in the above-identified patent and that said Letters Patent is hereby corrected as shown below:

Column 1,
Line 3, please insert
-- STATEMENT OF GOVERNMENT RIGHTS
Some of the work disclosed in this application was supported in part by grants from the National Science Foundation - grants DMI-9531255-10/96-9/99; DMI-0078548-10/00-9/03; DMI-010907. The United States Government may have certain rights in this invention. --

Signed and Sealed this

Twenty-sixth Day of April, 2005

JON W. DUDAS
*Director of the United States Patent and Trademark Office*